(12) United States Patent
Lichtenauer et al.

(10) Patent No.: US 12,239,377 B2
(45) Date of Patent: Mar. 4, 2025

(54) OPHTHALMOLOGICAL IMAGING METHOD, DEVICE AND SYSTEM

(71) Applicant: MEDMONT INTERNATIONAL PTY LTD, Nunawading (AU)

(72) Inventors: Paul Lichtenauer, Nunawading (AU); Robert Heavyside, Nunawading (AU)

(73) Assignee: MEDMONT INTERNATIONAL PTY LTD, Nunawading (AU)

( * ) Notice: Subject to any disclaimer, the term of this patent is extended or adjusted under 35 U.S.C. 154(b) by 605 days.

(21) Appl. No.: 17/439,060

(22) PCT Filed: Mar. 16, 2020

(86) PCT No.: PCT/AU2020/000019
§ 371 (c)(1),
(2) Date: Sep. 14, 2021

(87) PCT Pub. No.: WO2020/181315
PCT Pub. Date: Sep. 17, 2020

(65) Prior Publication Data
US 2022/0151487 A1      May 19, 2022

(30) Foreign Application Priority Data
Mar. 14, 2019 (AU) .............................. 2019900848

(51) Int. Cl.
*A61B 3/107* (2006.01)
*A61B 3/14* (2006.01)
*A61B 3/00* (2006.01)

(52) U.S. Cl.
CPC .............. *A61B 3/107* (2013.01); *A61B 3/14* (2013.01); *A61B 3/0075* (2013.01); *A61B 3/0083* (2013.01)

(58) Field of Classification Search
CPC ......... A61B 3/107; A61B 3/14; A61B 3/0075; A61B 3/0083; A61B 3/152; A61B 3/0033; A61B 3/0008; A61B 2576/02
USPC ......................................................... 351/206
See application file for complete search history.

(56) References Cited

U.S. PATENT DOCUMENTS

| | | | |
|---|---|---|---|
| 6,152,565 A | 11/2000 | Liu et al. | |
| 6,447,119 B1 | 9/2002 | Stewart et al. | |
| 2003/0231283 A1 | 12/2003 | Mura | |
| 2008/0018856 A1 | 1/2008 | Sarver et al. | |
| 2008/0297724 A1 | 12/2008 | Shimizu et al. | |
| 2009/0161067 A1* | 6/2009 | Youssefi | A61F 9/008 351/205 |
| 2009/0175525 A1* | 7/2009 | Farrer | G01B 11/2513 382/131 |
| 2013/0093998 A1 | 4/2013 | Bishop | |
| 2015/0131055 A1 | 5/2015 | Catanzariti et al. | |
| 2016/0143524 A1 | 5/2016 | Berard et al. | |

(Continued)

FOREIGN PATENT DOCUMENTS

| | | | |
|---|---|---|---|
| JP | H02206425 A | | 2/1990 |
| JP | 2022524881 A | * | 5/2022 |

(Continued)

*Primary Examiner* — Mohammed A Hasan
(74) *Attorney, Agent, or Firm* — Sunit Talapatra; Foley & Lardner LLP

(57) ABSTRACT

An ophthalmological topographer is disclosed. The ophthalmological topographer includes a corneal topographer and a scleral measurement device including one or more scleral projection systems. Methods of determining topography are also disclosed.

26 Claims, 17 Drawing Sheets

(56) References Cited

U.S. PATENT DOCUMENTS

2017/0042421 A1* 2/2017 Wallace ................ A61B 3/107
2018/0125355 A1 5/2018 Mrochen et al.

FOREIGN PATENT DOCUMENTS

| WO | 2007042854 A1 | 4/2007 |
| WO | 2016123448 A2 | 8/2016 |

* cited by examiner

OPHTHALMOLOGICAL IMAGING METHOD, DEVICE AND SYSTEM

CROSS-REFERENCE TO RELATED APPLICATIONS

This application is the United States national phase of International Application No. PCT/AU2020/000019 filed Mar. 16, 2020, and claims priority to Australian Patent Application No. 2019900848 filed Mar. 14, 2019, the disclosures of each of which are hereby incorporated by reference in their entireties.

The present invention relates to an ophthalmological imaging method, device and system. More particularly this invention relates to an ophthalmological imaging method, device and system comprising a multi-function light guide and scleral measuring system.

BACKGROUND TO THE INVENTION

Corneal topographers measure the geometry of the anterior corneal surface by capturing an image of the reflections from the cornea of a known illuminated target pattern, imaged on the eye as one or more mires, typically a series of concentric illuminated annuli separated by a black opaque annuli known as a Placido system and analysing these starting from the known location of the corneal apex. A separate system is required to determine the distance from a known reference location of the imaging system to said corneal apex.

Known corneal topographers direct light across the profile of the cornea and, via one or more mirrors and a lens system, forms an image of the profile on an imaging sensor. This profile imaging system allows the location of the corneal apex to be measured at the same time as an image of the target reflections was acquired.

Scheimpflug topography and other projection type topographic systems and lately OCTs have been applied to corneal and scleral mapping. With the Scheimpflug method, the high intensity light used for the retina typically results in the sclera becoming blurred. Further disadvantages of Scheimpflug systems are the high cost of instruments and long capture time, which results in loss of accuracy and thereby requires complex registration methods. The application of low intensity light to the sclera and high intensity light for the retina has been investigated, with referencing of the two through the limbus. Projection systems and OCTs can lack in accuracy at the important central corneal region, and uneconomic for many users in this field.

Alternative and improved corneal topographers and devices for mapping the cornea and sclera as well as effectively adding additional diagnostic features to a topographer are needed to meet the increasing demands in the market.

The reference to any prior art in this specification is not, and should not be taken as, an acknowledgement or any form of suggestion that the prior art forms part of the common general knowledge.

SUMMARY OF THE INVENTION

The present invention is directed to an ophthalmological imaging method, device and system.

In one broad form, the invention is directed to an ophthalmological imaging method, device and system comprising a multi-function light guide.

In another broad form, the invention relates to an ophthalmological topography light guide which illuminates the eye. In yet another broad form, the present invention relates to an ophthalmological topography light guide or cone which illuminates the eye and transmits light for capture.

In a first aspect, although it need not be the only or indeed the broadest form, the invention provides a light guide for an ophthalmological topographer, the light guide comprising:
  a light guide body comprising a reference object; and
  a topography illumination source illuminating the light guide body and the reference object wherein the illuminated light guide body directs light for illumination of said eye.

The illuminated light guide body according to the first aspect may also direct the reference object onto said eye surface. The directed reference object onto the eye surface may comprise a projected reference object or mires.

The light guide of the first aspect may further comprise:
  a directing optical system housed in a proximal end of the light guide body directing light from the light guide body across said corneal profile; and
  a reflecting optical system housed in the proximal end of the light guide body reflecting light from the directing optical system that has traversed the corneal profile through the light guide body.

The reflecting optical system may direct light to one or more capture system comprising at least one imaging sensor. The one or more capture system and/or at least one imaging sensor may be external to the light guide body.

In a second aspect, the invention provides an ophthalmological topographer comprising:
  a light guide body comprising a reference object;
  a topography illumination source illuminating the light guide body and the reference object wherein the illuminated light guide body directs light for illumination of said eye; and
  an imaging system imaging the reference object projected onto said eye surface through a central channel in the light guide body.

In a third aspect, the invention provides an ophthalmological topographer comprising:
  a light guide body comprising a reference object;
  a topography illumination source illuminating the light guide body and the reference object wherein the illuminated light guide body directs light for illumination of said eye;
  an imaging system imaging the reference object projected onto said eye surface through a central channel in the light guide body;
  a directing optical system housed in a proximal end of the light guide body directing light from the light guide body across said corneal profile; and
  a reflecting optical system housed in the proximal end of the light guide body reflecting light from the directing optical system that has traversed the corneal profile through the light guide body.

The imaging system according to any one of the above aspects may comprise one or more lens. The imaging system may direct light onto one or more capture system.

The reflecting optical system according to any one of the above embodiments may reflect light for capture on the at least one imaging sensor.

In a fourth aspect, the invention relates to a light guide for an ophthalmological topographer, the light guide comprising:

a light guide body comprising a reference object wherein the light guide body guides light towards the reference object.

The light guide according to the fourth aspect may further comprise a topography illumination source illuminating the light guide body and the reference object wherein the illuminated light guide body directs light for illumination of said eye.

The light guide body according to any one of the above aspects may further comprise a substantially symmetrical shape and/or comprise a contoured profile at a proximal end. The contoured profile may comprise symmetrical and opposed extensions and recesses to obtain close proximity of the eye to a reference object and hence a large eye coverage. The extensions may house said directing optical system and said reflecting optical system. The extensions and/or recesses may be disposed at opposing points at the proximal end on the light guide body. The extensions and/or recesses may comprise a scalloped edge.

According to any one of the above aspects, at least a part of the directing optical system and at least a part of the reflecting optical system may be disposed on opposing sides of the light guide body. In one embodiment the directing optical system is disposed on a left hand side with respect to an operator and the reflecting optical system is disposed on a right hand side with respect to an operator. In other embodiments, the directing optical system is disposed on a right hand side, top or bottom with respect to an operator and the reflecting optical system is disposed on a left hand side, bottom or top, respectively with respect to an operator.

According to any one of the above aspects, the directing optical system and the reflecting optical system reflect light substantially at a right angle, and both propagation direction vectors intercept the axis of the central channel at a right angle.

According to any one of the above aspects, the light guide body may comprise a directing optical system housing and a reflecting optical system housing. The directing optical system housing and the reflecting optical system housing may be disposed in respective and opposed extensions.

The topographer according to any one of the above aspects may further comprise one or more capture system. The one or more capture system may comprise at least one imaging sensor such as a CCD (charge-coupled device) or CMOS (complementary metal-oxide-semiconductor (CMOS) image sensor. The one or more capture system may comprise a topography capture system and a profile capture system. The topography capture system may be used in topography utilising the reference object. The profile capture system may be used in eye profiling utilising light directed by the reflecting optical system. In another embodiment the one or more capture system comprises at least one imaging sensor for both topography and eye profiling.

The ophthalmological topographer according to any one of the above aspects may further comprise:
one or more optical systems for imaging said eye.

The one or more optical systems may be disposed in an optical path for imaging said eye.

In embodiments when the one or more optical systems comprise two or more optical systems, the topographer may further comprise a locator for selectively locating each of the optical systems comprised in the two or more optical systems in the optical path. Each of the two or more optical systems may comprise interchangeable optical systems in an optical path for imaging said eye.

The locator may comprise a wheel on which may be located each of the two or more interchangeable optical systems. The wheel may comprise one or more indexing location for precise positioning of each of the two or more optical systems. The locator may comprise a backlash free locator. The locator may comprise one or more teeth. The wheel may comprise a gear. The locator may comprise one or more actuator such as, a motor.

The wheel may comprise one or more fenestration for the central topography system.

In one embodiment of any one of the above aspects, the topographer comprises a lighting array comprising the topography illumination source and a profile optics illumination source. The topographer illumination source may comprise a distributed light source. The distributed light source and the profile optics illumination source may be resolvable or distinguishable. The distributed light source and profile optics illumination source may emit light at sufficiently different wavelengths so no interference in their corresponding imaging paths occurs.

The distributed light source may comprise a plurality of LEDs. The distributed light source may emit a broadband visible spectrum. Each of the plurality of LEDs may comprise an RGB LED. Each RGB LED may comprise an individual narrow waveband. Each of the plurality of LEDs may produce white light. The plurality of LEDs may comprise an array arranged in a particular embodiment as two or more rings of LEDs. The two or more rings of LEDs may be comprised on a printed circuit board.

The profile optics illumination source may emit infra-red light. The profile optics illumination light source may comprise a point light source. In one embodiment, the profile optics illumination light source is a LED.

In yet another embodiment of any one of the above aspects, a portion of an optical path of the distributed light source, and a portion of an optical path of the profile optics illumination source illuminates said eye surface.

The topography illumination source and/or profile optics illumination source may be disposed at a distal end of the light guide body.

In one embodiment of any one of the above aspects, the reference object comprises a plurality of annuli. The reference object may comprise a Placido disk comprising a plurality of concentric annuli. The plurality of concentric annuli may comprise alternating transparent and opaque annuli. The transparent annuli may be illuminated. The transparent annuli may be integral with the light guide body. The concentric annuli may be disposed along a length of an interior surface of the light guide body. The reference object may comprise an overlay comprising opaque annuli. The opaque annuli may be arranged linearly separated by transparent sections. The reference object may be painted or otherwise disposed on the light guide body. The painting or other application may comprise application of only the opaque annuli.

In another embodiment of any one of the above aspects, the light guide body may comprise a plurality of segments, each segment comprising a respective transmission coefficient. The transmission coefficient may be selected to provide an even illumination along a length of the reference object. Each segment may comprise any number of transparent annuli and opaque annuli. Each light guide segment may comprise an optically isolating external surface or cover. In one embodiment, one segment may be coloured to provide a visual target. In another embodiment one segment, or the light guide body, comprises a coloured filter to provide a visual target. The coloured segment or coloured filter may be green. The coloured filter may comprise polymeric film in the optical path. The visual target or target segment may be disposed at a distal end of the light guide body. The visual target or target segment may transmit coloured light. The light guide body may comprise two, three, four, five, six, seven, eight, nine or ten segments. In one embodiment the light guide body comprises three segments. The number of segments may be selected to provide adequate illumination.

In yet another embodiment of any one of the above aspects, the light guide body may comprise an optical medium with a transmission coefficient different to air for light propagation.

In another embodiment of any one of the above aspects, the light guide body comprises a substantially conical or toric shape. The substantially conical shape may comprise a frusto-conical shape. The conical or toric shape may comprise an internal channel. The external surface may comprise a curved or toric shape and the internal channel may comprise a substantially conical shape.

In yet another embodiment of any one of the above aspects, the light guide body is illuminated to a selective colour dependent on the light emitted by the lighting array. The light emitted by the lighting array may comprise white, red, green, blue or infra-red light. The visual indication of modality may comprise a light pulse or different brightness or intensity for a selected colour. The light pulse may be changed in frequency, modulation or duration. The brightness or intensity may change with modality.

In yet another embodiment of any one of the above aspects, the directing optical system and the reflecting system are positioned on substantially opposing points of the light guide body.

The directing optical system may comprise one or more prism disposed between the light source and exposed eye. The prism may comprise a diffusing prism.

The reflecting optical system may comprise one or more mirrors.

In another embodiment the directing optical system may comprise a mirror and the reflecting optical system may comprise a prism.

In another embodiment of any one of the above aspects, the light guide body comprises a transparent media. The transparent media may comprise one more optically homogeneous and transparent media. The media may comprise an acrylic such as Poly(methyl methacrylate) (PMMA).

In yet another embodiment of any one of the above aspects, light targeted by the reflecting optical system is incident on a profile imaging system disposed at a distal end of the light guide body.

In another embodiment of any one of the above aspects, the profile imaging system comprises one or more of a focusing lens system and an optical filter only transmitting light from the profile optics illumination source.

In yet another embodiment of any one of the above aspects, the profile imaging system focuses the targeted light onto the one or more capture system. The focused targeted light comprises information on the distance of the subject eye from a reference point.

In still another embodiment of any one of the above aspects, the profile imaging system focuses the profile plane of said eye onto the one or more capture system.

The interior surface and exterior surface of the light guide body may be polished. The polishing may achieve desired reflection compared to remaining scatter of propagating light of the light source.

In still another embodiment of any one of the above aspects, part of a profile optical path is comprised within the light guide body. The profile optical path, and the internal profile optical path, may comprise the directing optical system and the reflecting optical system. The directing optical system directs light across said eye profile to the reflecting optical system. The reflecting optical system directs light to the focusing optical system and/or the one or more capture system.

In another embodiment of any one of the above aspects, light from the topography illumination source follows two or more optical paths through the light guide body. The two or more optical paths may comprise two or more of: light rays that are completely coupled out of the light guide body; light rays that are partially coupled out of the light guide body and partially incident upon an eye; and light rays that are wholly incident on eye. In embodiments wherein the light guide body exterior surface is painted or otherwise coated, the light rays that are completely coupled out of the light guide body may be absent. The light rays incident on the eye may then traverse said central channel and be incident on the one or more capture system.

According to any one of the above embodiments, the reflecting optical system and the directing optical system for imaging the eye profile are comprised in a profile system.

In yet another embodiment of any above aspect, the light guide body comprises the reference object; the profile system; and the light guide body provides the necessary optical input to image the topography of the corneal surface.

In still another embodiment of any one of the above aspects, the light guide body comprises at least a part of a central topography system comprising, the light guide body; the topography illumination source; the reference object and the topography imaging system. The central topography system may further the one or more capture system.

According to any one of the above embodiments, the ophthalmological topographer may comprise a corneal topographer. According to this embodiment the eye surface comprises the corneal surface; the eye profile comprises the corneal profile; the illumination of the eye may comprise illumination of the cornea; and the eye coverage may comprise corneal coverage.

According to any one of the above aspects, the topographer may further comprise a scleral measurement device. The scleral measurement device may comprise one or more scleral projection systems. Each of the one or more scleral projection systems may comprise a scleral projection light source and a scleral reference object.

Each scleral reference object may comprise at least one diaphragm comprising one or more apertures. The one or more apertures may be disposed in an aperture pattern. The one or more apertures may comprise a scleral aperture pattern and optionally a corneal aperture pattern. When imaged on the eye or the at least one imaging sensor the scleral aperture pattern may be imaged as one or more scleral locators and the corneal aperture pattern may be imaged as a corneal scatter image.

Each of the one or more scleral projection systems may further comprise a scleral projection imaging system. The scleral projection imaging system may comprise one or more lens.

The one or more scleral projection system may be symmetrically mounted on the topographer. The symmetrically mounted scleral projection system may comprise a scleral projection system mounted on either side of the topographer. In one embodiment a scleral projection system is disposed on either side or both sides of the light guide, i.e. a symmetrically mounted left scleral projection system and a symmetrically mounted right scleral projection system. This allows for projection of the aperture pattern onto different portions of said eye surface.

The scleral aperture pattern illuminated by the scleral projection light source may be imaged onto the projection imaging system and onto said scleral portion of said eye surface. The corneal aperture pattern illuminated by the projection light source may also be imaged onto the projection imaging system and onto the cornea.

The scleral measurement device may further comprise one or more scleral registration reference object projector. The scleral registration reference object projector may comprise a scleral reference light source and a scleral registration reference object. The scleral reference object may comprise a registration reference object light guide which optionally may be provided in the form of two or more concentric rings and may comprise a second Placido disk.

Light coming from the scleral reference light source and passing through the scleral registration reference object may be reflected from said eye surface and imaged through the imaging system onto the one or more image capture system.

The light from the scleral reference light source passing through the scleral registration reference object and reflected from said eye surface may form a scleral image. The scleral image may be digitally processed to obtain corneal height information and scleral locations and comprising scleral height information.

The processed scleral image may be used to combine the corneal height information from the topographer with the scleral height information into a new scleral topographic map. The combination may comprise image registration. Registration may utilise one or more of the scleral locator; the corneal scatter image; and the scleral registration reference image.

The at least one diaphragm may comprise two or more adjacent registration apertures through which light from the scleral reference light source can propagate and be disposed onto the cornea. In one embodiment the two or more adjacent registration apertures comprise respective sets of one or two or more adjacent transparent round dots. In another embodiment the adjacent registration apertures comprise a set or two or more adjacent transparent and opaque alternating rings concentric to the axis of the central channel, forming a second Placido disk. In a particular embodiment, the two or more adjacent apertures comprise three transparent circular rings. In yet another embodiment, the three transparent circular rings may be used as a reference diaphragm and can be used together with the alternating transparent and opaque annuli.

The projected scleral aperture pattern on the eye surface and the registration diaphragm may be imaged together on the same image onto the one or more capture system. From such two adjacent locators or dots of the said registration diaphragm, curvature and height information of the reflecting eye surface can be derived.

The one or more scleral reference object apertures and/or the scleral registration apertures may be imaged on the one or more imaging sensor by the imaging system.

The scleral measuring device may further apply an algorithm to improve the accuracy of the scleral height information by comparing an eye reference axis of the scleral image to an eye reference axis of a corneal image. Said reference axis may contain rotational information of the eye to the axis of the central channel or between the eye and the central channel.

In one embodiment, the light guide body and topography illumination source may form the corneal reference object.

In a preferred embodiment, the corneal reference object comprises both a corneal reference object projected by the light guide body and topography illumination source for an apical point and the corneal aperture pattern for the for additional corneal reference information.

In yet another embodiment, said pupil may be captured in both the scleral and corneal image wherein the captured pupil information may provide information of said eye reference axis for additional corneal reference information.

In still another embodiment, other uniquely identifiable scleral features may be used to combine said corneal and scleral height information.

In another embodiment, the pupil centre location of the eye relative to the said axis of central channel may be measured to provide reference data for combining said corneal and scleral height information.

In a fifth aspect the invention provides a method of determining ophthalmological topography comprising:
    illuminating a light guide body comprising a reference object to project a reference object onto an anterior surface of said cornea, wherein the illuminated light guide body projects light for illumination of said cornea;
    directing light from the light guide body across said corneal profile using a directing optical system housed in a proximal end of the light guide body;
    reflecting light from the directing optical system that has traversed the corneal profile through the light guide body with a reflecting optical system housed in the proximal end of the light guide body;
    capturing the reflected light on the at least one imaging sensor external to the light guide body; and
    capturing the reference object projected onto said corneal surface through a central channel in the light guide body to determine corneal topography.

The method of the fifth aspect may further comprise:
    imaging an aperture pattern projected by one or more projection lens systems onto the eye surface wherein the aperture pattern projects at least one scleral reference objects and at least one corneal reference object; and
    combining the scleral height information to the determined corneal height information.

According to any one of the above aspects, the light guide may comprise a multi-function light guide. The multi-function may comprise an imaging function comprising disposing light to the eye for imaging the eye and a profile optical function comprising imaging the profile contour of said eye. The multi-function and imaging function may also comprise a topography optical function comprising imaging the topography of the eye.

According to any one of the above aspects, the light guide may comprise a topography cone.

According to any one of the above aspects, the topographer comprises one or more of a housing and a baseplate. The topographer may also comprise a subject rest comprising one or more of a chin rest and forehead rest. The topographer may further comprise an adjustment arm to move the chin rest up and down. The subject rest may also comprise a calibration device attachment to which a calibration device may be attached for calibrating topographer. The topographer may also comprise a manually operated positioner such as, a joystick. The manually operated positioned may move a base unit in two axes; sideways and forward-backward movement. The topographer may be also be moved vertically such as, by rotation of the joystick. The vertical movement may be through a mounting column on which the light guide and other components such as, the topography illumination source; profile imaging system; and topography imaging system are mounted.

According to any one of the above aspects, the topographer may be connected to junction box by a topographer cable. The junction box may be connected to a computer by a computer cable and to a power supply.

According to any one of the above aspects, the topographer may further comprise a printed wiring board for controlling the topographer and/or communication with the computer. The printed wiring board may be disposed on the mounting column.

According to any one of the above aspects, the topographer may also comprise an external illuminator. The external illuminator may provide light for the interchangeable optical systems. The external illuminator may comprise symmetrically mounted light sources. The symmetrically mounted light sources may be disposed at both sides of the light guide, i.e. symmetrically mounted left light source and a symmetrically mounted right light source. The light sources may be any suitable light source such as an LED.

The housing may a protective enclosure around one or more of the base unit; the vertical mounting column; at least part of the light guide body; the external illuminator; and parts of the scleral measuring device.

Further aspects and/or features of the present invention will become apparent from the following detailed description.

BRIEF DESCRIPTION OF THE DRAWINGS

In order that the invention may be readily understood and put into practical effect, reference will now be made to embodiments of the present invention with reference to the accompanying drawings, wherein like reference numbers refer to identical elements. The drawings are provided by way of example only, wherein:

FIG. 1A shoes a perspective view of the topographer and FIG. 1B shows a close up view of the cone and cone housing.

Figure 1A:
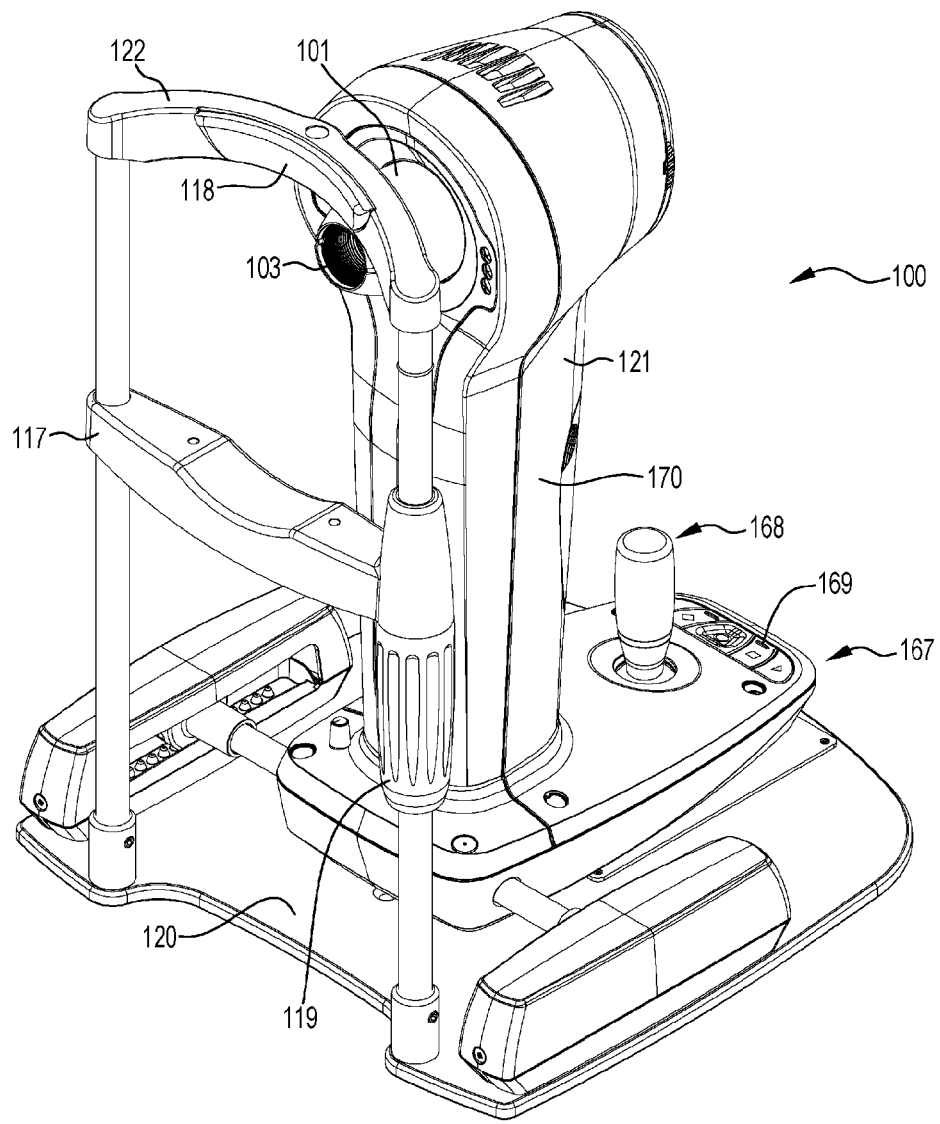
FIGS. 1A and 1B are schematic diagrams showing one embodiment of a corneal topographer according to the invention.

Skilled addressees will appreciate that elements in the drawings are illustrated for simplicity and clarity and have not necessarily been drawn to scale. For example, the relative dimensions of some elements in the drawings may be distorted to help improve understanding of embodiments of the present invention.

DETAILED DESCRIPTION OF THE INVENTION

Embodiments of the present invention relate to an improved ophthalmological topography light guide and an improved ophthalmological topographer. The skilled person will readily appreciate that a light guide, as used for topography, is also referred to as "a cone". This is because such light guides are conventionally conically shaped. The light guide of the present invention has an internal surface that is substantially conically shaped however, the external surface is not conically shaped. In view of convention and the terms used in the art, these terms light guide and cone may be used interchangeably herein.

The inventors have surprisingly discovered that by comprising a reference object integrally within a light emitting corneal topography light guide, the reference object may form part of the light guide body and the imaging system. This is of significant advantage because the light guide body may be smaller and the light guide function can be provided by the light guide body which is more cost effective and allows additional imaging modes and increased performance of corneal topography. Another advantage of one embodiment of the invention is that profile optics can be provided in the light guide body.

In another embodiment, the present invention provides multi-function topography through the provision of an interchangeable lens system that is backlash free. The ability to use individual lenses for each interchangeable system optical system means more control can be exercised over each lens design and the overall quality can be improved.

Additionally, the ophthalmological topographer provides for the first time, scleral topography capability and methodology. This is done whilst maintaining the high quality of corneal topography and which may be combined with the additional data of scleral topography. This may lead to better quality and improved contact lens fitting. Also, fluorescein is not required to obtain topographical information of the cornea or sclera, which is of great advantage to the user and is beneficial to subject comfort when compared to the prior art.

As used herein an "optical system" means one or more lenses or other image forming components, mirror, prism, spectral optical filter and/or or aperture for directing, observing, analysing, recording and/or capturing light. It is to be understood that a particular optical system may be comprised of different arrangements of one or more lens or other image forming components, mirror, prism, spectral optical filter and/or aperture and perform the same function. For example, where a particular optical system is described herein as comprising one or more prism it is to be understood that a different construction comprising one or more lens or other image forming components, mirror, prism, spectral optical filter and/or apertures may be substituted for the prism.

As used herein, an "imaging system" means a specific type of optical system, that forms a real or virtual image of an object.

As used herein a "mire" is a pattern of a reference object whose image, as reflected by the curved surface of the cornea, is used in calculating the topography of the cornea.

From the description below it will become clear that the light guide or cone of the invention is a multi-function light guide or cone. As used herein "multi function light guide or cone" is used to refer to a light guide or cone performing more than one optical function. In one embodiment, the multi-function light guide body directs light and mires onto to the eye for imaging the mires imaged on the eye onto an imaging sensor and further comprises a profile optical system for imaging the profile contour of said eye.

Generally, one embodiment of the present invention relates to a cone or light guide body comprising a reference object for a topographer.

In another embodiment, the invention relates to a light guide or cone comprising a reference object, a profile optical system for imaging a profile of an eye and a topography optical system imaging the corneal surface with the illuminated reference object 103 imaged as mires on the eye and onto the imaging sensor.

As will be elucidated below, in one embodiment the invention also provides an interchangeable optical system, to allow the performance of more than one operating modality and imaging function.

One embodiment of a topographer 100 according to the invention is shown in FIG. 1. Topographer 100 comprises a topography light guide or cone 101 accommodated in housing 121. Sturdy support is provided by baseplate 120. A stable platform is provided by subject rest 122 which comprises chin rest 117 and forehead rest 118. An adjustment arm 119 is also provided for moving chin rest up and down. This vertical adjustment allows for different head sizes to be aligned accurately so the height of the eye 106 is lined up with the optical axis of topographer 100.

Topographer 100 is connected to junction box 160 (not shown) by topographer cable 214. The junction box 160 is in turn connected to a conventional computer 161 (not shown) by computer cable 162 (not shown) inserted into a USB (universal serial bus) port and to a power supply 163 (not shown) by power cable 164 (not shown).

Subject rest 122 also comprises a calibration device attachment 165 (not shown) to which a calibration device 166 (not shown) may be attached for calibrating topographer 100.

Topographer 100 also comprises a manually operated positioner 167 comprising a joystick 168 which may be used to move base unit 169 in two axes; sideways and forward-backward movement. Additionally, vertical movement is accomplished by rotation of joystick 168. This allows accurate and convenient alignment of topographer 100 with the subject's eye 106. The vertical movement is through mounting column 169 on which the light guide 101 and other components such as, the light guide lighting array 155, profile imaging system 112 and topography imaging system 123 are mounted.

As will be described in further detail below, topographer 100 also comprises external illuminator 207 which provides additional light for topography and for additional ophthalmic imaging functions. The external illuminator 207 comprises light sources 208 which are symmetrically mounted at either side of the light guide 101. The light sources 208 may be any suitable light source such as an LED.

Also further described below is the optional provision of a scleral measurement device 400 comprised in some embodiments of topographer 100. Scleral measurement device 400 comprises one or more scleral projection systems 401 and scleral reference object 402 shown in FIGS. 10 and 11A. The scleral measurement device may further comprise one or more scleral registration reference object projector 404.

Also as described below in further detail, the imaging system 123 also comprises one or more actuator 307 (not shown), such as a motor, that rotates wheel 302 to a defined position for alignment in the imaging system optical path.

Figure 1B:
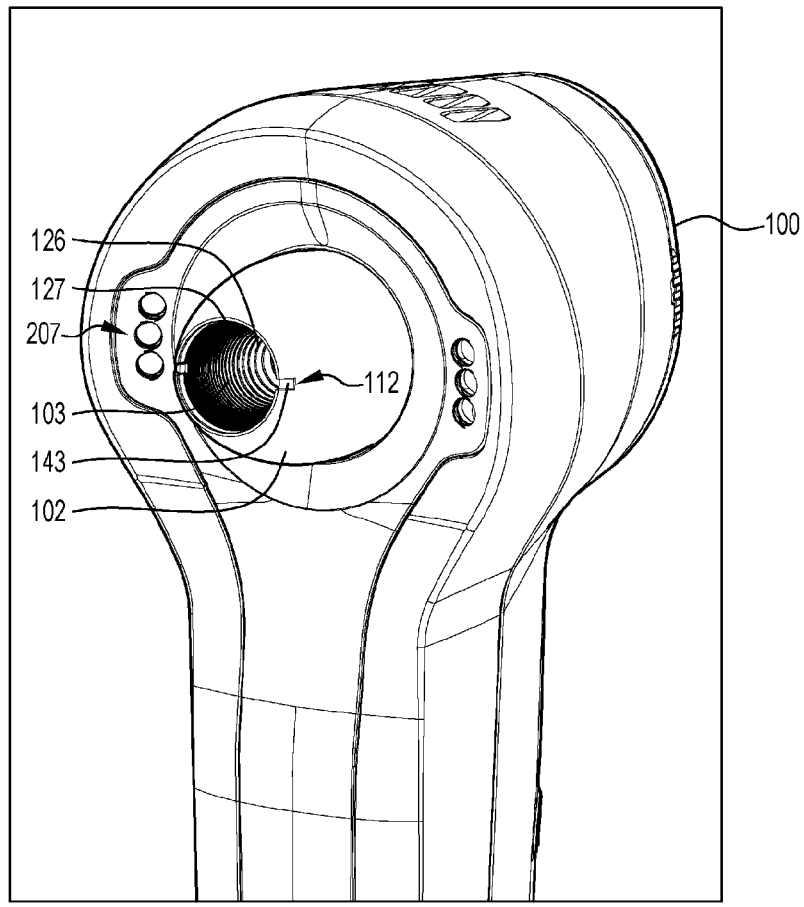

Also disposed on the mounting column 169 is a printed wiring board 170 (not shown) used for controlling the topographer 100 and communication with the computer 161. As shown in FIG. 1A and FIG. 1B all the internal components are enclosed in housing 121 which forms a protective enclosure around the base unit 169 and the vertical mounting column 170. Additionally, light guide body 102 is partially enclosed within housing 121.

FIG. 1B shows light guide 100 and part of the profile imaging system 112. Light guide 100 comprises a light guide body 102 which comprises at least a part of reference object 103 which is illuminated to image the topography annuli or rings as mires 126.

Light guide body 102 is comprised of a transparent media 104. In the embodiment shown in FIG. 2 the transparent media 104 comprises poly(methyl methacrylate) (PMMA). Based on the teaching herein, a skilled person is readily able to select any other suitable transparent media. The transparent media 104 may comprise one more optically homogeneous and transparent media.

Light guide body 102 comprises a substantially toric or conical external surface 142 shape and a substantially conical inner surface 141 shape. In the embodiment shown in the Figures, the substantially toric or conical shape is a torus or frusto-conical shape comprising central channel 124. The diameter of cone 101 decreases along its length from distal end 115 to proximal end 109. The toric or conical shape means that the distal end diameter is greater than the proximal end diameter so that the concentric transparent annuli 128 and opaque annuli along the length of light guide body 102 reduce in circumference from the distal end 115 to the proximal end 109.

Light guide body 102 is dimensioned conveniently to fit the human form of the face, with an orifice diameter of the central channel of less than 35 mm, and an overall diameter of the light guide body 102 of less than 70 mm and a length of the light guide body 10 of less than 100 mm. The depth of the topographer 100 is less than 300 mm and the height of the topographer 100 is less than 450 mm.

In another embodiment light guide body 102 is substantially symmetrical and comprises a contoured profile 125 (not shown) at proximal end 109. The contoured profile 125 comprises symmetrical and opposed extensions 145 (not shown) and recesses 146 (not shown). The extensions 145 house at least a part of the directing optical system 108 and at least a part of the reflecting optical system 111. Extensions 145 are disposed at opposing points at the proximal end 109. The recesses 146 are also disposed at opposing points at the proximal end 109. The extensions and recesses may comprise a scalloped edge.

In another embodiment of any one of the above aspects, at least a part of the directing optical system and at least a part of the reflecting optical system are located opposite each other on the proximal end of light guide body. Significantly, the directing optical system directs light at a right angle to the optical axis.

Light guide 101 is attached to the topographer 100 through a mounting flange 147 (not shown). The toric or conical shape of the light guide body 102 housing central channel 124 permits exposure of eye 106 to reference object 130 disposed on the interior surface 141.

FIG. 1B shows a front perspective view of part of topographer 100 showing a close up of the region comprising the light guide 101 and making the reference object 103 visible through the central channel 124.

Figure 2A:
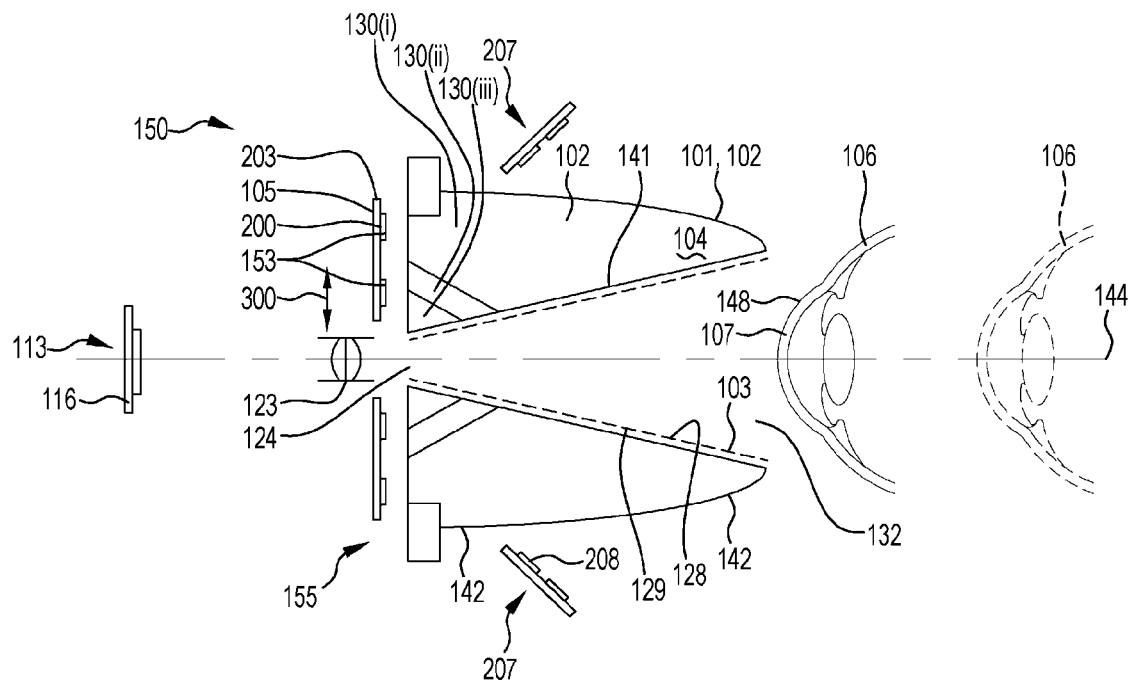
FIGS. 2A and 2B are schematic diagrams showing sectional views of one embodiment of a topographer of the invention.

As shown in the perspective view of FIG. 1B and the section view of FIG. 2A, reference object 130 comprises a plurality of annuli or rings in the form of alternating transparent annuli 128 and opaque annuli 129 (represented as dashed lines in the section view of FIG. 2A). In the embodiment shown, reference object 130 comprises a plurality of transparent annuli 128, each adjoined on both sides by an opaque annulus 129, disposed on interior surface 141 along its axial length. Terminal annuli 128, 129 will only be adjoined by a counterpart annuli 129, 128 on a non-terminal side.

When light guide 101 is illuminated, the plurality of transparent annuli 128 are illuminated and form a virtual image of concentric rings as mires 126 produced by the curvature of the anterior corneal surface 148. By imaging and analysing the imaged concentric ring mires 126 produced by the anterior corneal surface 148 through the imaging system 123 resultant from transparent annuli 128, the topography of the cornea 107 may be determined. In this respect and in this embodiment, reference object 103 may be referred to as a Placido disk.

The interior surface 141 faces central channel 124. The interior surface 141 and exterior surface 142 of the light guide body 102 may be polished so as to act as a reflective or refractive optical surface.

The transparent annuli 128 are integral with the light guide body 102. In the embodiment shown, reference object 103 is, or more accurately, the opaque annuli 129 are, painted or otherwise applied onto light guide body 102. In another embodiment, the painting, or other application, may comprise application of opaque annuli 129 and transparent annuli 128. In still another embodiment, reference object 103 may comprise an overlay 149 (not shown) comprising a transparent sheet 151 on which the opaque annuli 134 are comprised. In this embodiment, opaque annuli 129 may be printed on the sheet 151. The overlay 149 is then positioned inside central channel 124 so that the printed opaque annuli 129 extend along the length of the channel 124.

In the embodiment shown in FIGS. 1A and 1B, reference object 103 comprises thirty transparent annuli 128. From the teaching herein a skilled person is readily able to select other suitable reference objects and other suitable numbers of mire producing features. For example, reference object 103 may comprise 5 to 50, 10 to 40 or 20 to 35 transparent rings or other mire producing feature.

Figure 8A:
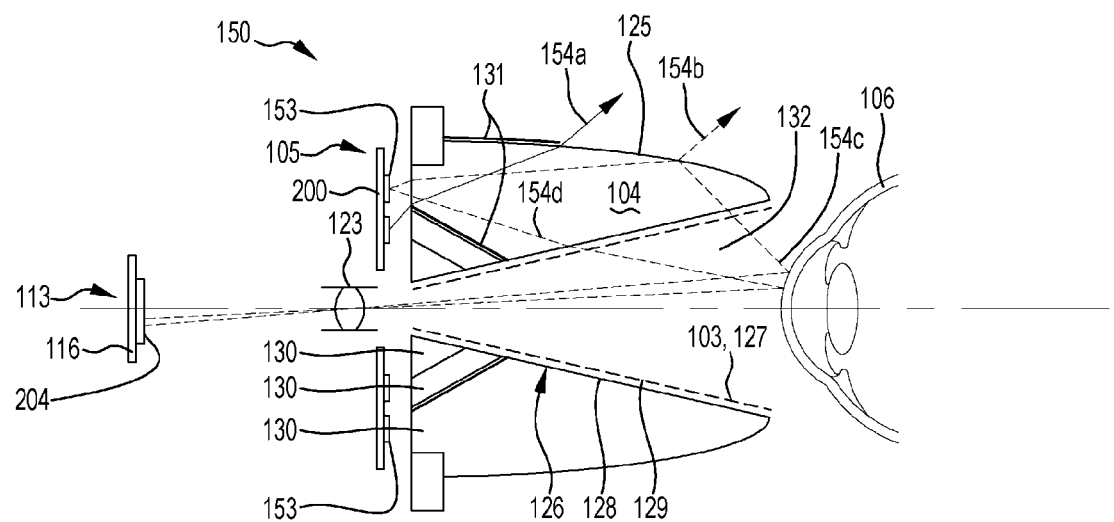
FIGS. 8A and 8B are schematic diagrams showing a sectional view illustrating corneal topography lights paths (FIG. 8A) and corneal profile light paths (FIG. 8B) according to one embodiment of the invention.

FIGS. 2A and 8A, also show that in order to provide even illumination of the rings 126, light guide body 102 may be comprised of a plurality of light guide segments 130, In the embodiment shown in FIGS. 2A and 8A, light guide body 102 comprises three segments 130$i$, 130$ii$ and 130$iii$. Each segment 130 comprises a respective coupling efficiency matched to provide even illumination of each transparent annuli 126 along the length of the reference object 103. Each segment 130 may comprise any number of transparent annuli 128 and opaque annuli 129.

In other embodiments, light guide body 102 may comprise one, two, four, five, six, seven, eight, nine, ten segments or more than ten segments 130. The number of segments 130 may be selected to provide adequate illumination.

In the embodiment shown, each segment 130 comprises a coupling efficiency to produce an evenly illuminated ring image on the at least one imaging sensor 1116.

Importantly, light guide body 102 comprises a higher coupling efficiency compared to that of radiation of the topography illumination source 105, including the distributed illumination source 200 and profile optics illumination source 201, into free space.

As shown in FIG. 8A, each light guide segment 130 and part or all of the exterior surface 142 may comprise an optically isolating cover 131 to prevent leaking light into the other light guide segments and or prevent or reduce light coupling out of the light guide body 102.

Segment 130($i$) comprises a target segment which may be coloured or otherwise comprise a visible indicia to provide a target for the gaze of eye 106 looking through channel 124. In the embodiment shown, although not visible in the black and white figures, target segment 130($i$) is coloured green. Target segment 130($i$) is shown disposed at a distal end of light guide body 102. All other segments 130($i$),($ii$) may be of the same transparent material but different from 130($i$) in dimension and coupling efficiency, and preferably clear.

Figure 2B:
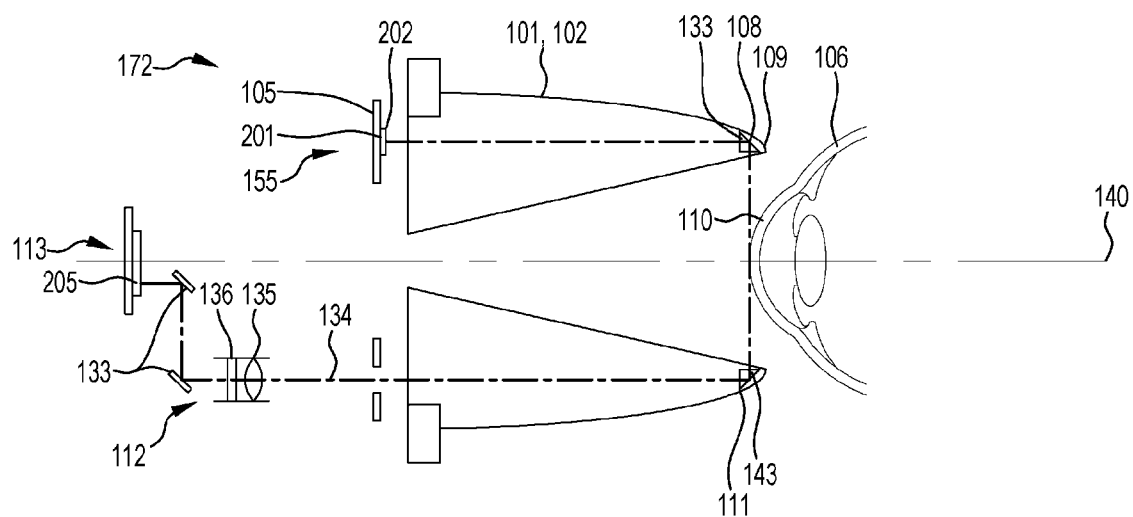

FIG. 2A shows the components for corneal topography according to one embodiment of the invention, while FIG. 2B shows the components for profile imaging according to one embodiment of the invention. Further explanation is provided by FIGS. 8A and 8B which show the optical paths for the central topography optical system 150 and the profile system 172, respectively.

As shown in both FIGS. 2A and 2B, illumination of topographer 100 is provided by light guide lighting array 155 which comprises a topography illumination source 105 (FIG. 2A) and a profile optics illumination source 201 (FIG. 2B). Light guide body 102 is illuminated by topography illumination source 105. Significantly, the topography illumination source 105 and the profile optics illumination source 201 are resolvable. The topography illumination source 105 and profile optics illumination source 201 may emit light at sufficiently different wavelengths so no interference occurs of the images on the at least one imaging sensor 116.

Topography illumination source 105 illuminates reference object 103 or at least the transparent annuli 128. That is, the topography illuminations source 105 illuminates light guide body 102 to provide light for illumination of the cornea 107 and for projection of reference object 103 onto the anterior corneal surface 148.

Topography illumination source 105 comprises a distributed illumination source 200 and thereby comprises a plurality of separate illumination sources in the form of topography illumination LEDs 153, which emit polychromatic or white light. The plurality of LEDs 153 are comprised in two or more concentric rings of LEDs 153 comprised on a printed board (PCB) 203. Although no corresponding figure is provided, in the embodiment shown, topography illumination source 105 comprises an outer ring 105(a) and inner ring 105(b).

FIG. 8A shows three optical paths of light emitted by the topography illumination source 105 comprised of LEDs 153. Some light has an optical path such as, topography optical path 206a, and is entirely coupled out of the light guide body 102 from exterior surface 142. Other light partially takes topography optical path 206b in which light rays are partially coupled out of light guide body 102 from exterior surface 142 and partially takes topography optical path 206c in which it is reflected off the external surface 142 towards the interior surface 141 upon eye 106 before traversing central channel 124 to be incident on the at least one imaging sensor 116. That is, the light within the light guide body 102 can be divided at the exterior surface 142 and partially refracted and disposed to the surrounding environment. Optical path 206d shows light rays that do not pass the exterior surface 142 and traverse towards interior surface 141, are incident upon eye 106, before traversing central channel 124 and central imaging system 123 to be incident on the at least one imaging sensor 116 to form corneal image 204. That is, mires 126 are imaged on imaging sensor 116.

Turning to FIG. 2B, profile optics illumination source 201 is shown to comprise a profile point light source 202, in the form of a single LED, emitting infra-red light. The light from point light source 202 traverses light guide body 202 and is directed by directing optical system across the corneal profile 110 to be received by the reflecting optical system 111 and directed to the profile imaging system 112 for direction to capture system 113 and at least one imaging sensor 116 where profile image 205 is formed and captured.

Directing optical system 108 is shown to comprise a mirror 133 and reflecting optical system 111 is shown to comprise a prism 143. In other embodiments, this arrangement is reversed with the directing optical system 108 comprising a prism and reflecting optical system 111 comprising a mirror.

The profile imaging system 112 is shown to comprise mirrors 133 and other components to direct the light propagation direction vector 134 to capture system 113.

From FIGS. 2A and 2B it can bee see that imaging is performed with capture system 113 which is shown to comprise at least one imaging sensor 116. In other embodiments, capture system 113 comprises two or more imaging sensors, which may be provided in the form of a topography imaging sensor 173 (not shown) and a profile imaging sensor 152 (not shown).

FIG. 2A also shows that the relative position of light guide body 201 and eye 106 may be moved such as, with positioner 167. This is advantageous as it allows convenient positioning of eye 106 for each respective optical system 300a, 300b, 300c, 300d, comprised in the interchangeable optical system 300. In the embodiment shown in FIGS. 3A, 3B, 3C, and 3D, interchangeable optical system 300 is disposed on a locator 301 in the form of a wheel 302 which can rotate in each direction to accurately align each respective optical system 300a, 300b, 300c, 300d, in the central channel and with one or more capture system 113.

Figure 3A:
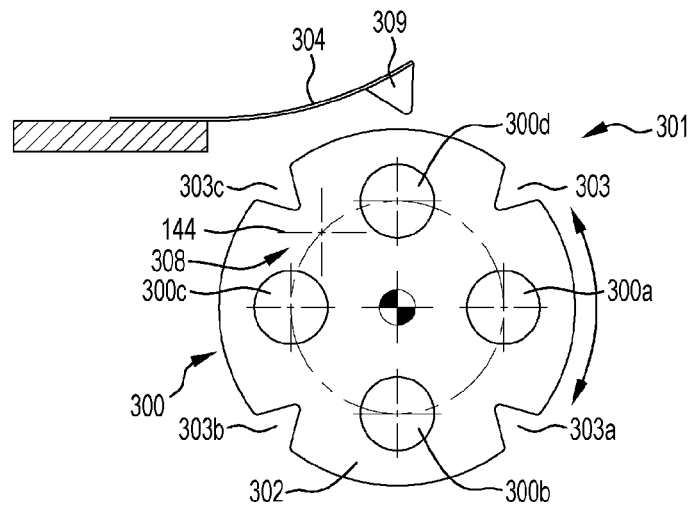
FIGS. 3A, 3B, 3C and 3D are schematic diagrams showing one embodiment of a locator for positioning the lens systems.

As shown in FIG. 3A, wheel 302 comprises a fenestration 308 for the axis of the central channel 144 for the central topography system 150.

Wheel 302 may be rotated in either direction, clockwise or counter-clockwise, as shown by the arrow on FIG. 3A.

Wheel 302 comprises indexing locations 303 which engages with one or more teeth. The one or more teeth 309, which in the embodiment shown in FIGS. 3A, 3B, 3C and 3D comprises a sole tooth, may be disposed on pivoting lever 305 which acts as a spring 304.

Wheel 302 comprises one or more indexing location 303 for precise positioning of each of the two optical systems. In the embodiment shown in FIGS. 3A, 3B, 3C and 3D, the interchangeable optical system 300 comprises four optical systems 300a, 300b, 300c, and 300d and four respective indexing locations 303a, 303b, 303c, and 303d. By selecting an appropriate indexing location 303a, 303b, 303c, 303d, for engagement with one or more teeth 309, a respective optical system 300a, 300b, 300c, 300d, may be accurately positioned with respect to the central channel 124 for imaging eye 106.

Figure 3B:
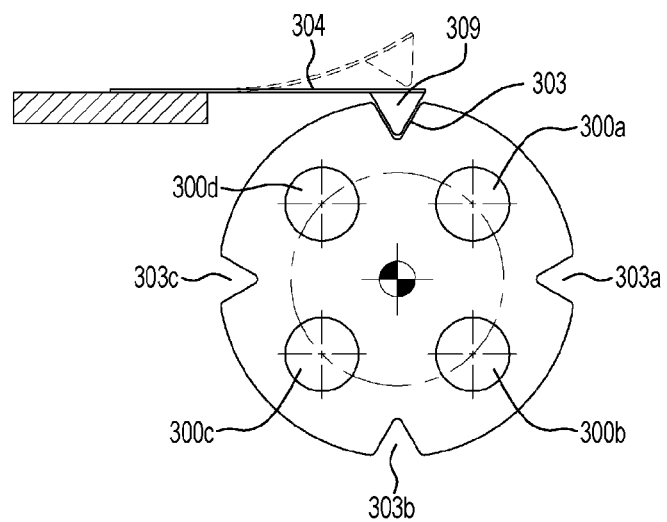
Figure 3C:
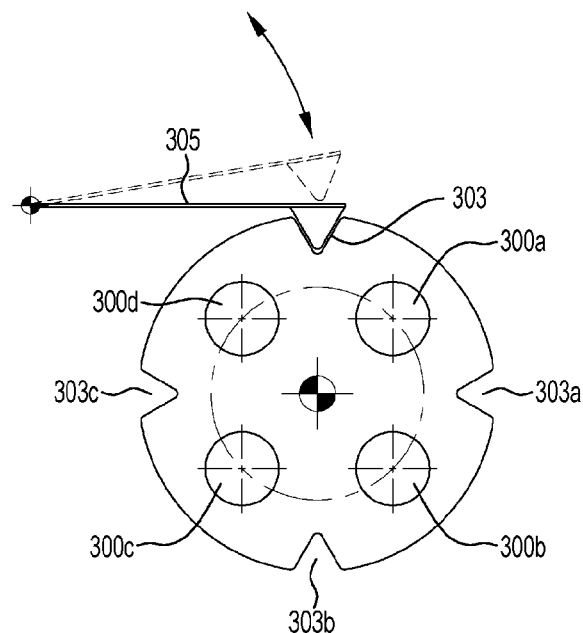

FIG. 3A shows the one or more teeth 309 not engaged with wheel 302 which is in transition between two indexing locations 303. FIG. 3B shows the wheel 302 having turned further so that the one or more teeth 309 is now engaged with when 302 and pivoting lever 305 has sprung back to engage with wheel 302.

Figure 3D:
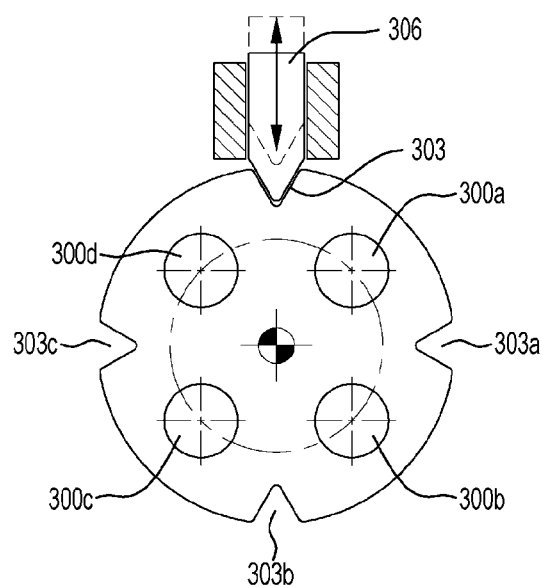

FIG. 3D shows another embodiment of locator 301 which instead of using a pivoting lever 305 uses a sliding element 306.

Although not shown, locator 301 further comprises one or more actuator 307 in the form of a motor 421 for effecting the rotation.

Figure 4:
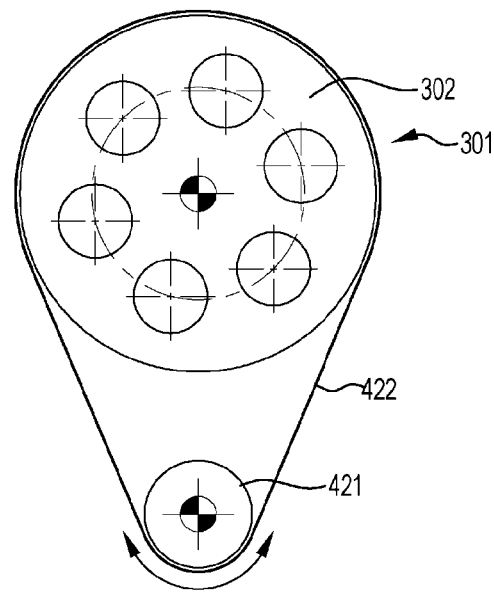
FIGS. 4A and 4B are schematic diagrams showing a locator according to another embodiment of the invention.

FIG. 4 shows another embodiment of locator 301 comprising a motor 421 which drives transmission belt 422 to effect rotation of wheel 302. In another embodiment, the wheel 302 comprises a gear.

In the embodiment shown in FIG. 3D the interchangeable optical system 300 comprises six optical systems. In other embodiments, two, three, five, seven, eight, nine, ten, or more than ten optical systems may be comprised.

Locator 301 is a backlash free locator which advantageously provides accurate location and prevents or at least reduces undesired movement.

Advantageously, the light guide body 102 is illuminated to a different colour dependent on the light emitted by the lighting array 155. The light emitted by the lighting array 155 may comprise different distinguishable colors which indicate a modality in use such as, central topography system 150, profile system 172, or a respective one of the interchangeable optical systems 300.

From the above a skilled person will appreciate that the visible light portion used for light propagation for the illumination of eye 106 can be split on its exterior surface and coupled out of the light guide body 102 to the surrounding areas and be visible to the user or patient. The coupled out light may also be used for illuminating the eye 106 in addition to other illumination means for imaging the eye 106 or surrounding areas of the eye 106 for imaging purposes.

The light coupled out and visible to the user or tested subject can contain information on the operating state of the topographer 100 or additional information. The information of the light may be presented in form of color as the preferred embodiment, but also can contain other light modulations like light pulses or changing brightness.

The light guide body 102 also provides a portion of the light path propagation for illumination of the corneal profile 110 and imaging of the corneal image 204 onto the at least one imaging sensor 116.

Figure 7A:
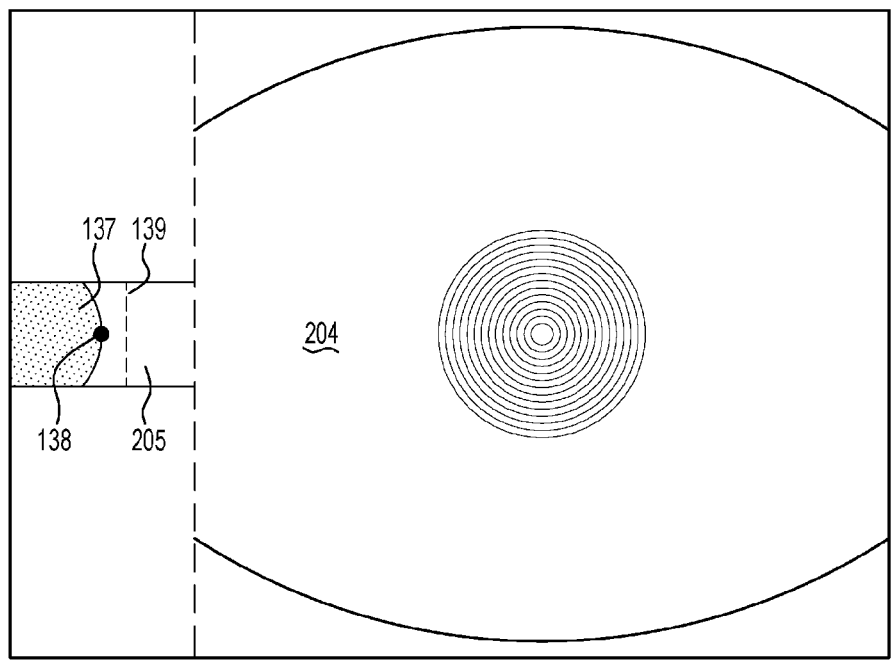
FIGS. 7A, 7B, 7C and 7D are diagrams showing: one embodiment of a profile image (left) and one embodiment of a corneal image (right) (FIG. 7A); a representation of the eye displaying an image of the reference object (FIG. 7B); a representation of the eye taken with illumination provided by the external illuminator (FIG. 7C); a representation of the eye with wearing a contact lens and visualised using fluorescein (FIG. 7D; and a representation of the eye showing the meibomian gland (FIG. 7E).

FIG. 7A shows a profile image 205 (left hand side) and a corneal image 204 (right hand side). FIG. 7A also shows that, advantageously, the profile data comprises profile contour 137 and apex location 138. A reference location 139 may be applied to determine the location of the eye 106 relative to the reference object 130 or to the central imaging system 123. These images 204, 205 are able to be reconstructed with the data captured from one or more capture system 113.

Figure 7B:
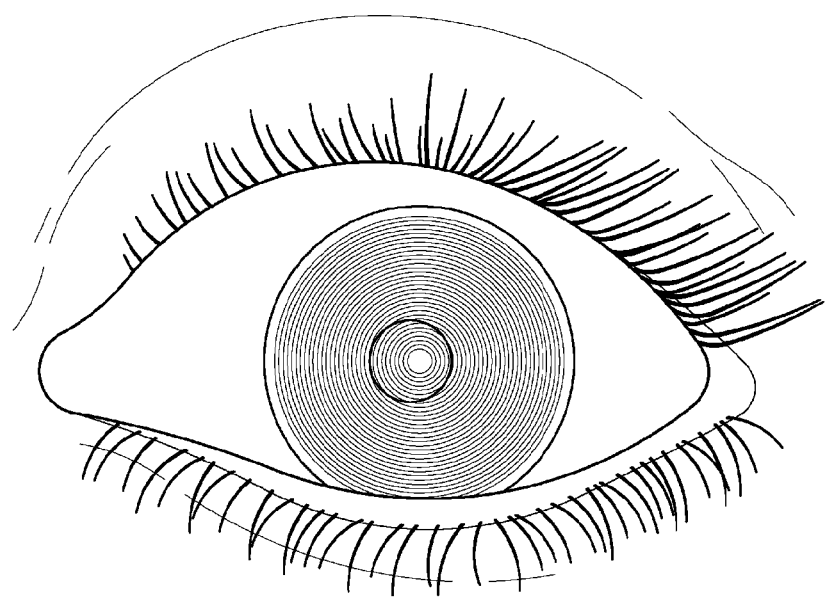
Figure 7C:
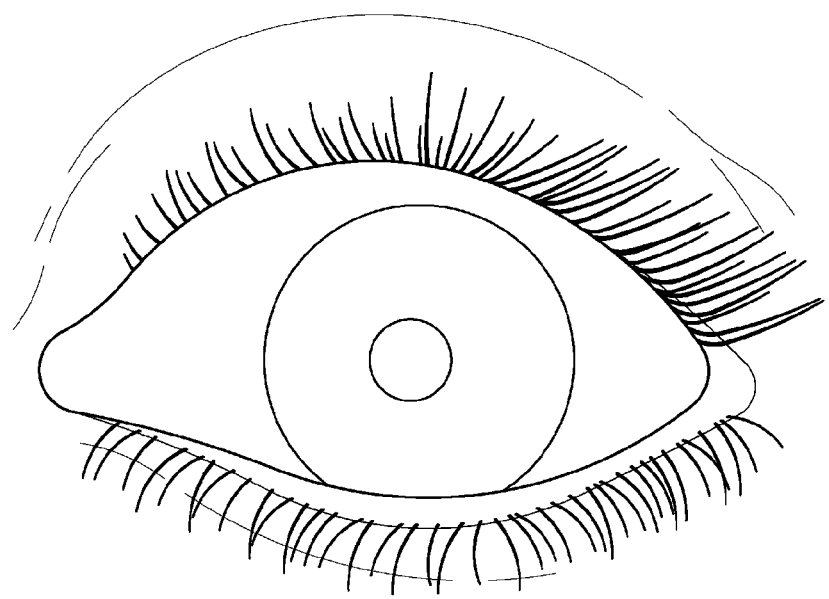
Figure 7D:
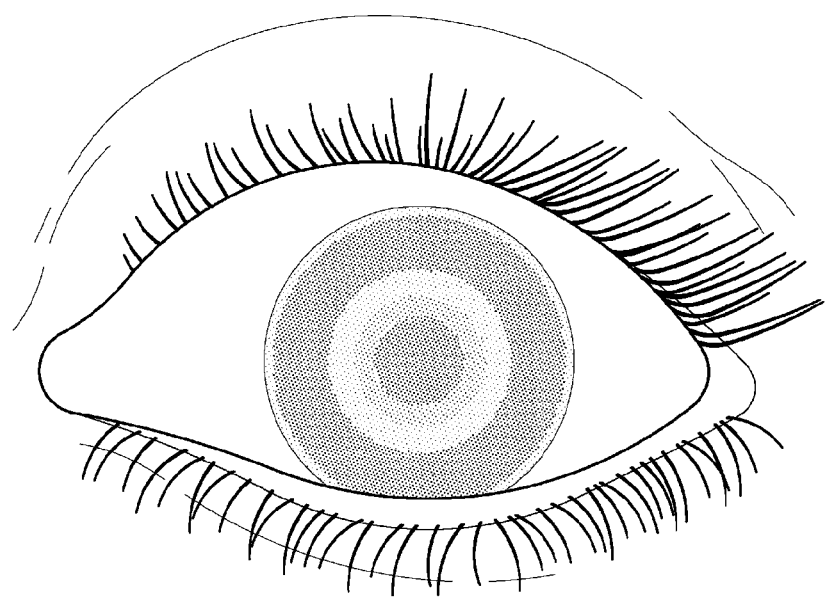
Figure 7E:
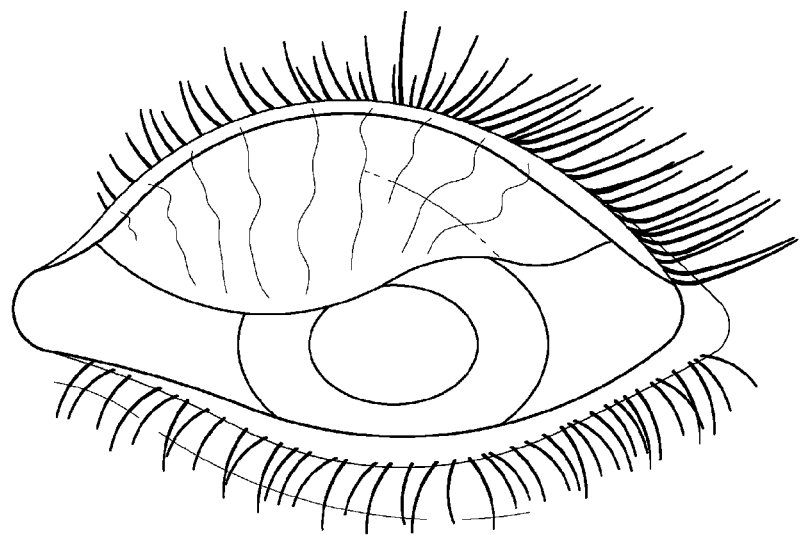

FIGS. 7B, 7C, 7D, and 7E show example information and images that may be obtained with the interchangeable optical systems 300. FIG. 7B shows an anterior image of the eye. FIG. 7C shows a corneal image. FIG. 7D shows a contact lens fitting image and FIG. 7E shows a meibomian gland image. FIGS. 7B, 7C, 7D, and 7E may for example be obtained with optical systems 300a, 300b, 300c, and 300d, respectively.

Another significant advantage of the interchangeable optical systems 300 is that each optical system 300a, 300b, 300c, 300d etc is complete and does not require any other imaging elements, in isolation or shared between each component interchangeable optical system 30a, 30b, 300c, 300d etc or from topographer 100 generally. This allows more than one imaging function to be performed.

Figure 5:
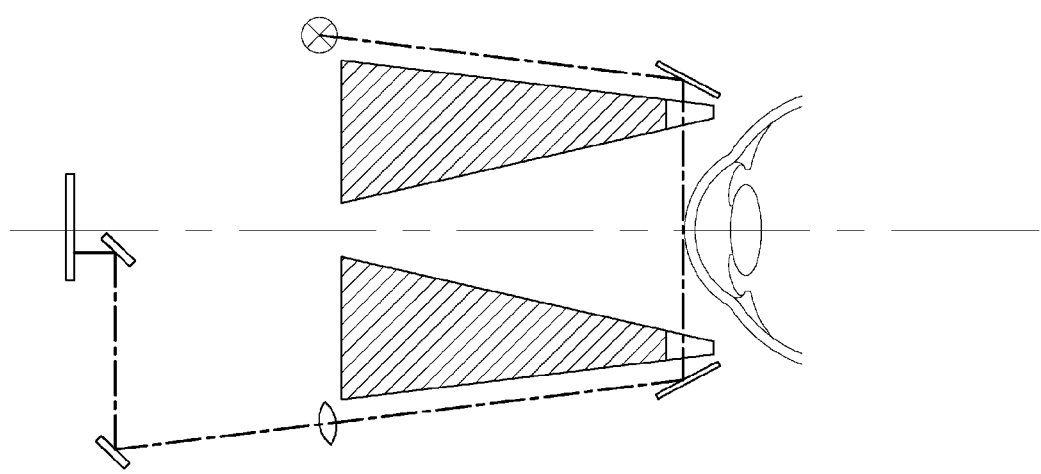
FIG. 5 is a schematic diagram showing a sectional view and light paths of a PRIOR ART device for acquiring corneal profile data.

FIG. 5 shows a schematic diagram of a prior art device for imaging a corneal profile. This sectional view shows that the prior art profile optics and the respective optical path is exterior, or mostly exterior, to the light guide body.

Figure 8B:
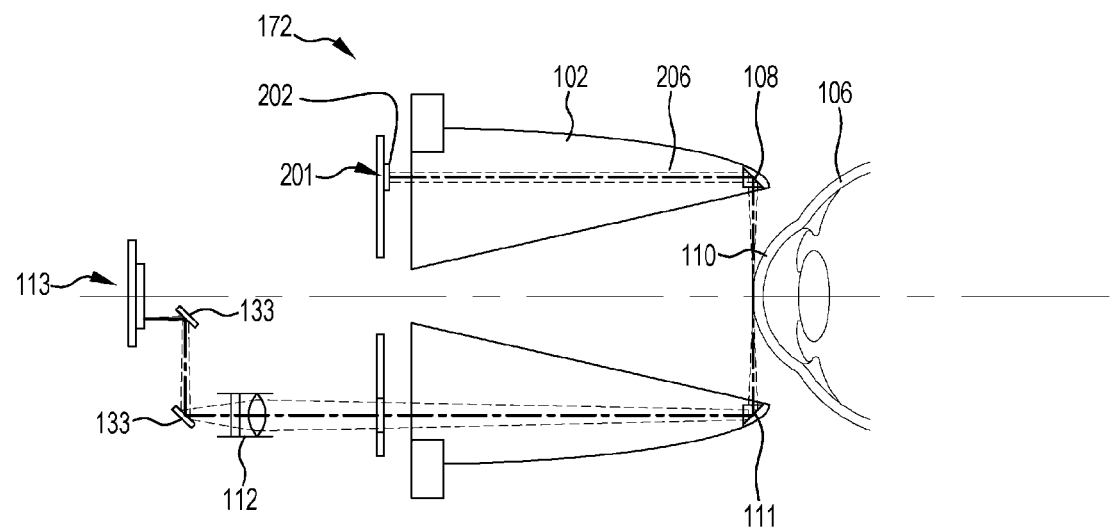

This contrasts with profile system 172 and profile optical path 206 shown in FIG. 8B which traverse the light guide body 102.

FIG. 8B shows, profile optical path 206 of light emitted by the profile optics illumination source 201. Light traverses through the transparent media 104 to the directing optical system 108 and reflecting optical system 111 mounted at opposing points on proximal end 109 of light guide body 102. The directing optical system 108 comprises a mirror 143 which directs the transmitted light across the corneal profile 110 along that part of the profile optical path 206 between mirror 143 and the prism 143 comprised in the reflecting optical system 111.

Reflecting optical system 111 reflects the directed light from the directing optical system 108 that has traversed the corneal profile 110 and targets it back through light guide body 102 to profile imaging system 112 and onto one or more capture system 113.

At least a portion of the light captured by directing optical system 108 is incident on reflecting optical system 111 disposed adjacent the distal end 110 of cone 100. The profile image 206 comprises information on the distance of the subject eye 190 from a reference point. The distance information is used together with the information comprised in the corneal image to obtain corneal curvature information. The distance information is derived by measuring the profile contour 137 of the profile image 205 and comparing its apex location 138 relative to a reference location on the profile image 205.

As shown in FIG. 2B, the profile imaging system 112 also comprise one or more focusing lens 135 to focus the profile plane of eye 106 onto the at least one imaging sensor 116. The profile imaging system 112 may be designed to correct for the optic path length through the light guide body 102.

Also shown in FIG. 2B is that profile imaging system 112 further comprises an optical filter 254 which only or substantially only transmits the infra-red light from the profile optics illumination light source 201.

The surfaces on the light guide body 102 used in the light propagation of the eye profile imaging are substantially perpendicular to the light propagation direction vector 134. That is directing optical system and reflecting optical system reflect light substantially at a right angle, and both propagation direction vectors intercept the axis of central channel at a right angle.

Figure 6:
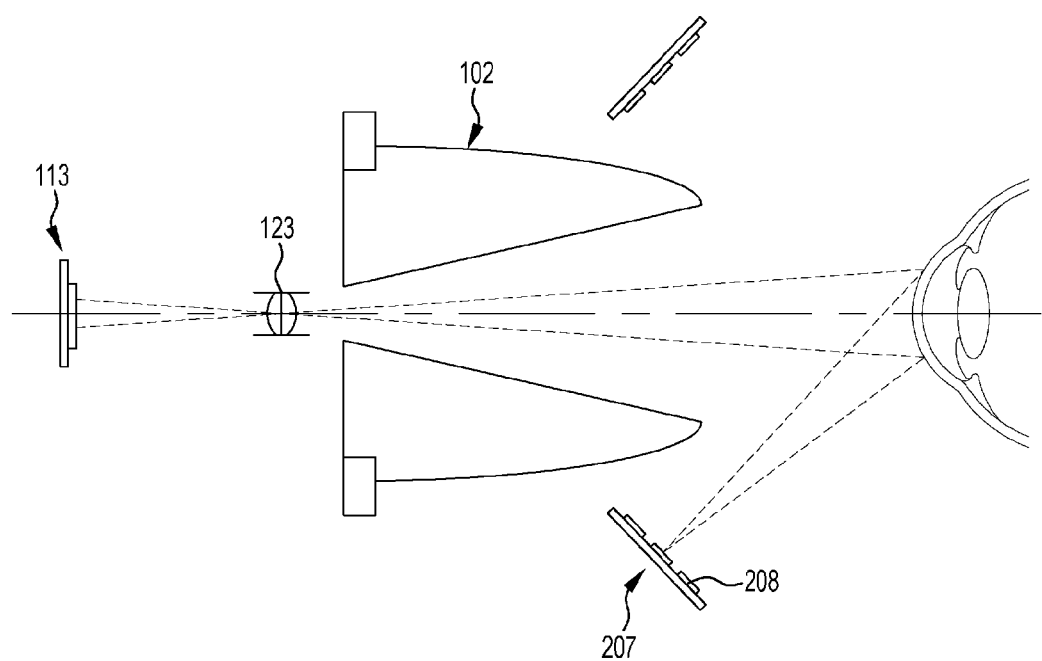
FIG. 6 is a schematic diagram showing another sectional view and light paths according to an embodiment of the invention for acquiring scleral data.

It may be desirable to provide additional light to the central topography system 105. FIG. 6 shows a schematic diagram of a cross section of topographer 100 showing the relative position of an external illuminator 207 with respect to the light guide body.

External illuminator 207 is outside the plane of the light guide body 102, and thereby positionally distinguished from centrally or internally positioned lighting array 155 and topography illumination source and profile imaging illumination source 201, which are in the same plane as light guide body 102.

Figure 9:
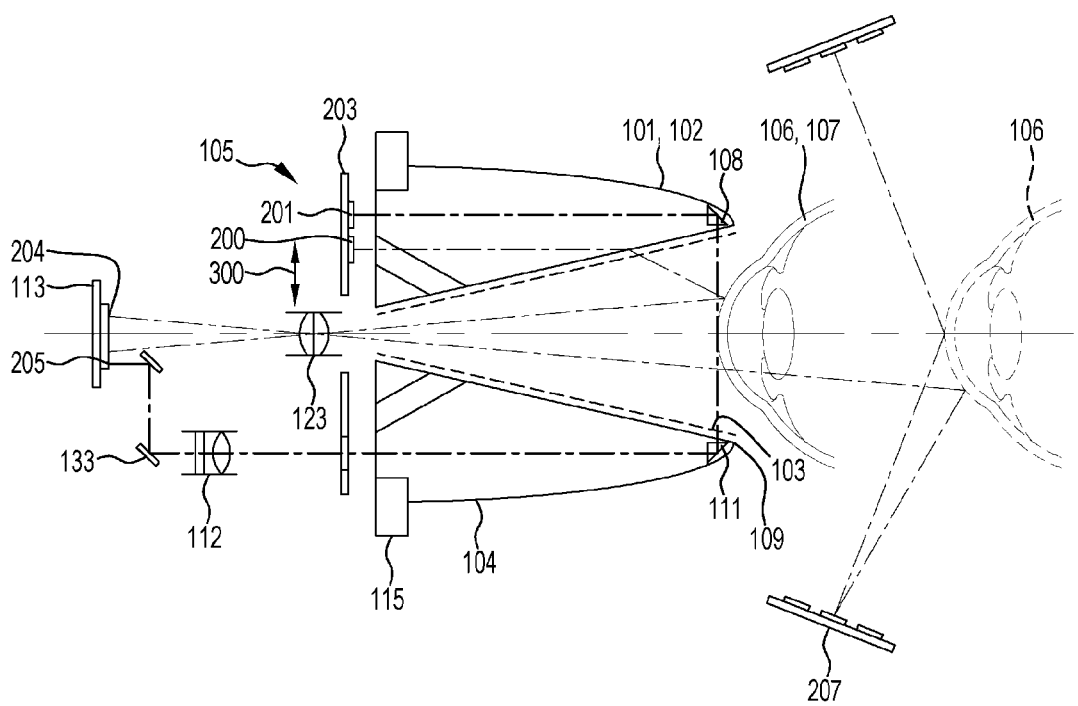
FIG. 9 is a schematic diagram showing a sectional view illustrating corneal topography and corneal profile light paths with additional external illumination according to one embodiment of the invention.

External illuminator 207 comprises light sources 208 which provide the additional illumination as shown in FIGS. 6 and 9. In the embodiment shown, light sources 208 comprise LEDs.

Figure 10:
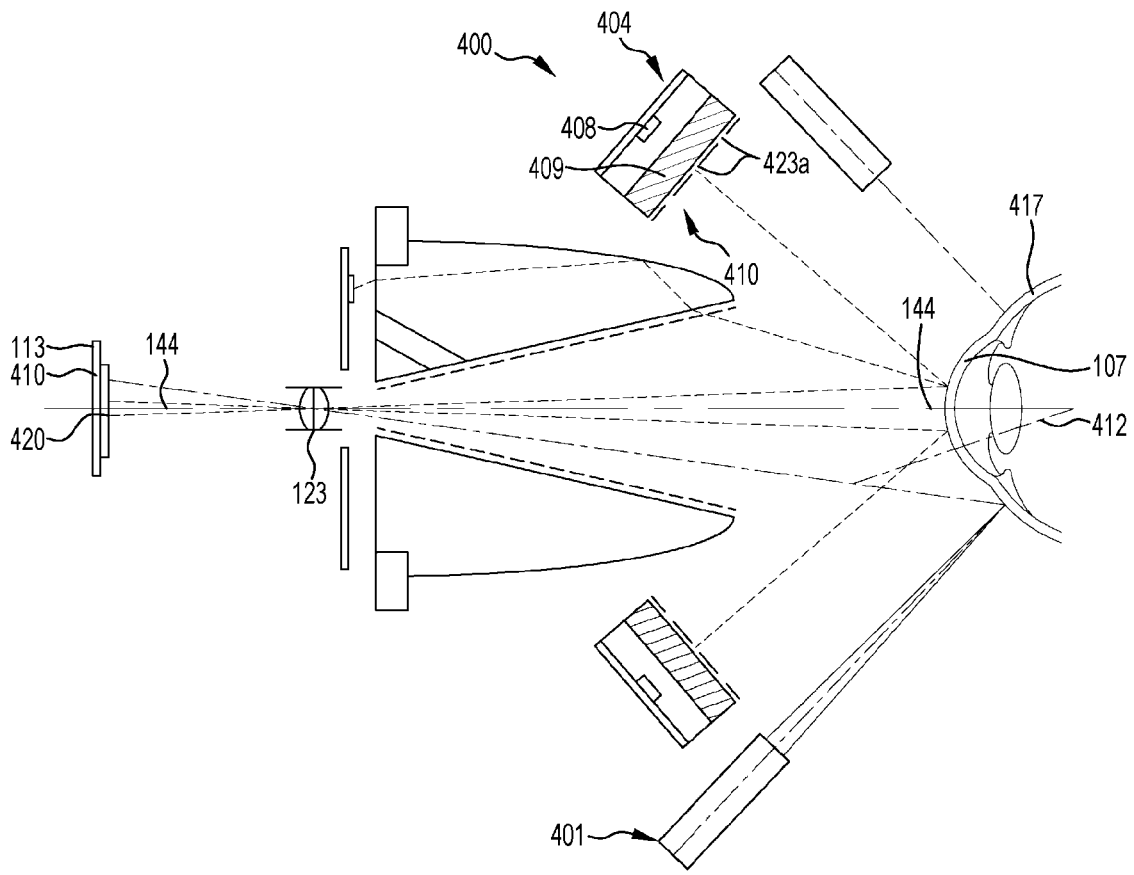
FIG. 10 is another schematic diagram showing a sectional view illustrating corneal and scleral topography lights paths according to one embodiment of the invention.
Figure 11A:
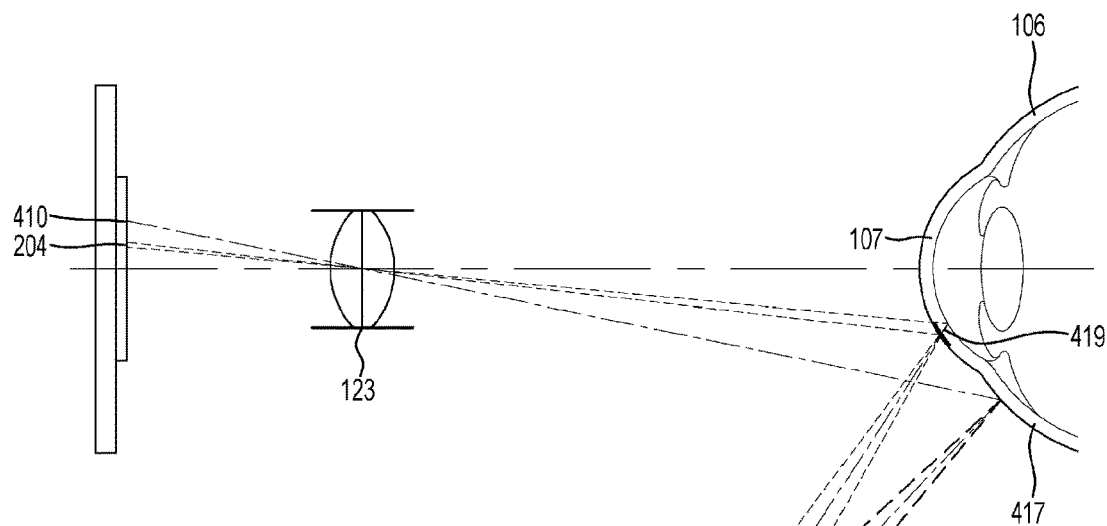
FIGS. 11A and 11B are schematic diagrams showing light paths for image registration according to one embodiment of the invention.
Figure 11B:
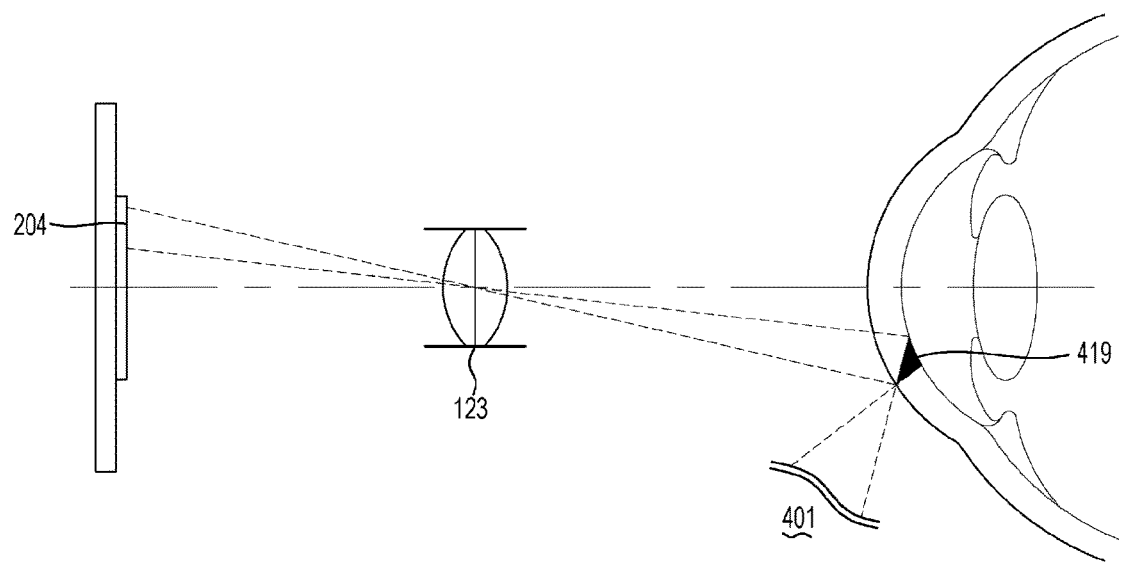
Figure 12A:
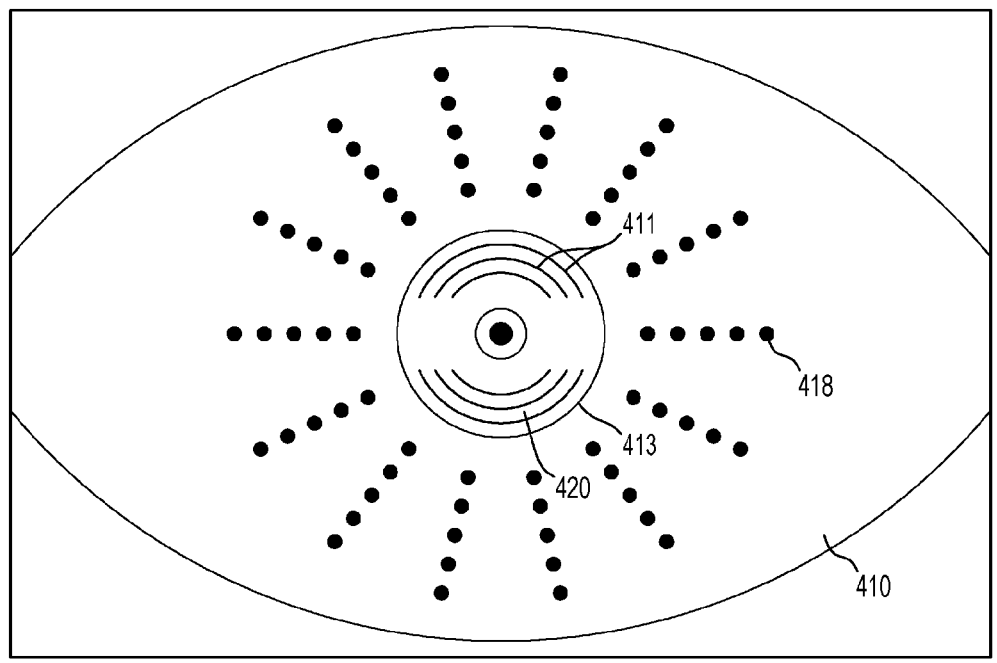
FIGS. 12A and 12B are schematic diagrams showing directed reference objects for image registration according to one embodiment of the invention.
Figure 12B:
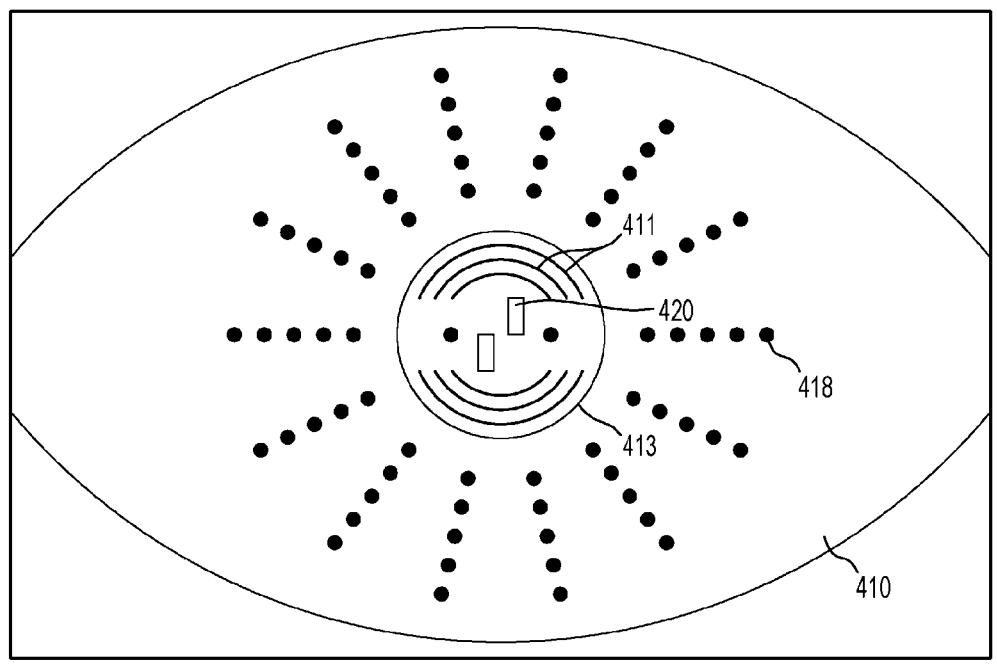

Turning to FIGS. 10, 11A and 11B, the topographer 100 may further comprise a scleral measurement device 400. The scleral measurement device 400 comprises one or more scleral projection systems 401, each of which comprise a scleral projection light source 406 and a scleral reference object 402.

The scleral reference objects 402 comprise at least one diaphragm 415 comprising one or more apertures 415a. The one or more apertures 415a are disposed in a scleral aperture pattern 405 and optionally a corneal aperture pattern 414. When imaged on eye 106 or the at least one imaging sensor 116 the scleral aperture pattern 405 may be imaged as one or more scleral locators 418 and the corneal aperture pattern 414 may be imaged as a corneal scatter image 419. As shown in FIG. 11A, the corneal scatter image 419 goes through the corneal so the measurement is through the eye in a volume scatter.

The one or more scleral projection systems 401 further comprise a scleral projection imaging system 403 which is shown to comprise one or more lens.

In the embodiment shown in FIG. 10, the one or more scleral projection systems 401 comprise two symmetrically disposed scleral projection systems 401, one mounted on each side of topographer 100. The symmetrically mounted scleral projection systems 401 may comprise a scleral projection system 401 mounted on either side of topographer 100. In one embodiment a scleral projection system 401 is disposed on either side or both sides of the light guide body 102, i.e. a symmetrically mounted left scleral projection system 401 and a symmetrically mounted right scleral projection system 401. This allows for projection of the aperture pattern 405, 414 onto different portions of said eye surface.

The scleral aperture pattern 405 illuminated by the scleral projection light source 406 may be imaged onto the scleral projection imaging system 403 and onto said scleral portion of said eye surface. The corneal aperture pattern 414 illuminated by the projection light source 406 may also be imaged onto the projection imaging system 403 and onto the cornea 107.

The scleral measurement device 400 further comprises one or more scleral registration reference object projector 404 which comprises a scleral reference light source 408 and a scleral registration reference object 407. The scleral registration reference object 407 may comprise a registration reference object light guide 409 which optionally may be provided in the form of two or more concentric rings and may comprise a second Placido disk. Light coming from the scleral reference light source 408 and passing through the scleral registration reference object 407 may be reflected from said eye surface and imaged through the imaging system 123 onto the one or more image capture system 113.

The light from the scleral reference light source 408 passing through the scleral registration reference object 407 and reflected from said eye surface forms a scleral image 410 which is digitally processed to obtain corneal height information and scleral locations and comprising scleral height information. A reader familiar with corneal topography understands, that height information and curvature information of the eye 106 are conjugate and contain the same information. The scleral height information and scleral curvature information may be converted from one to another by applying commonly known mathematical means.

The processed scleral image 410 may be used to combine the corneal height information from the topographer 100 with the scleral height information into a new scleral topographic map. The combination may comprise image registration. Registration may utilise one or more of the scleral locator 418; the corneal scatter image 419; and the scleral registration reference image 420.

Figure 13:
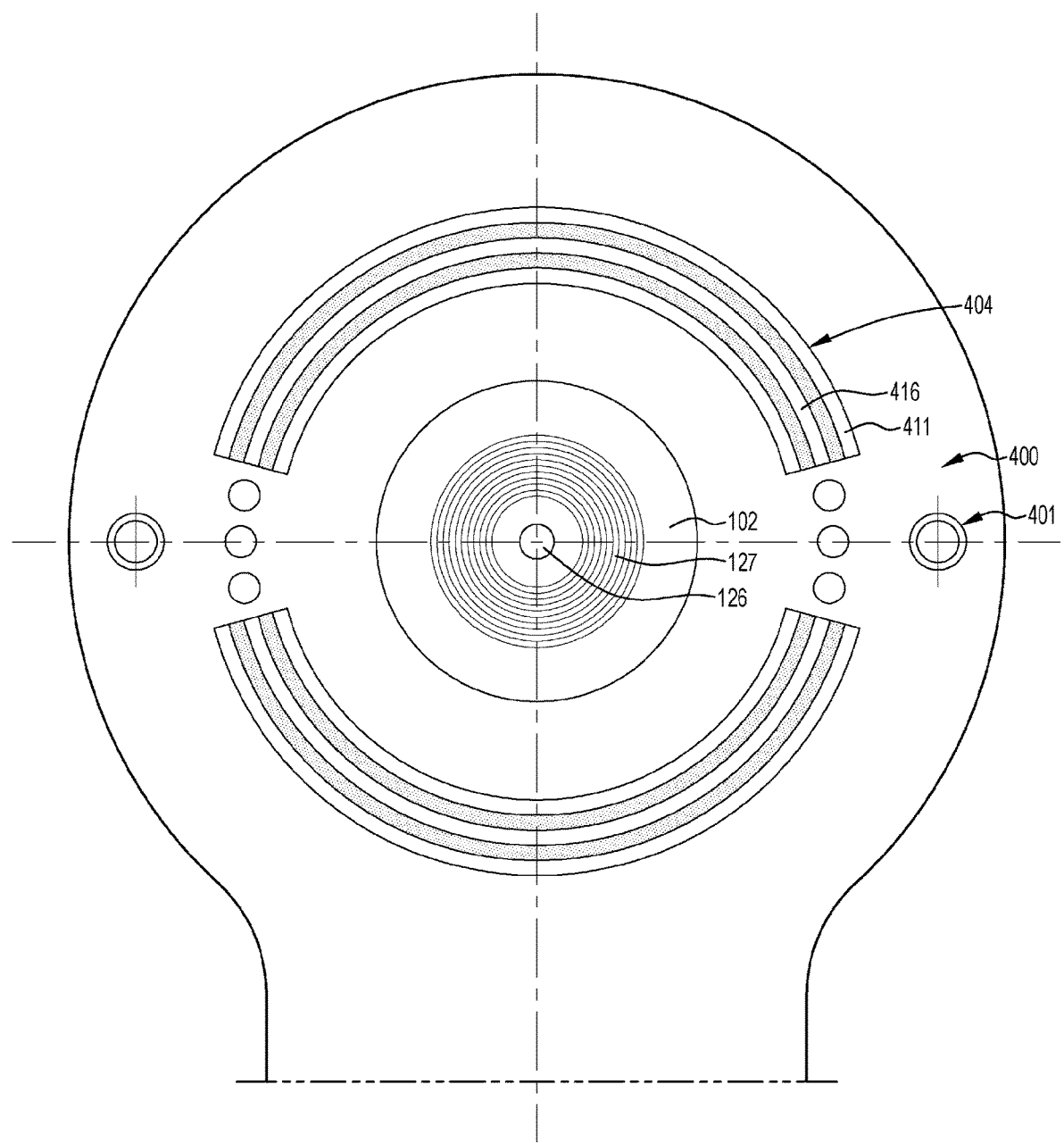
FIG. 13 is a schematic diagram showing a front view of a topographer according to one embodiment of the invention.
Figure 14A:
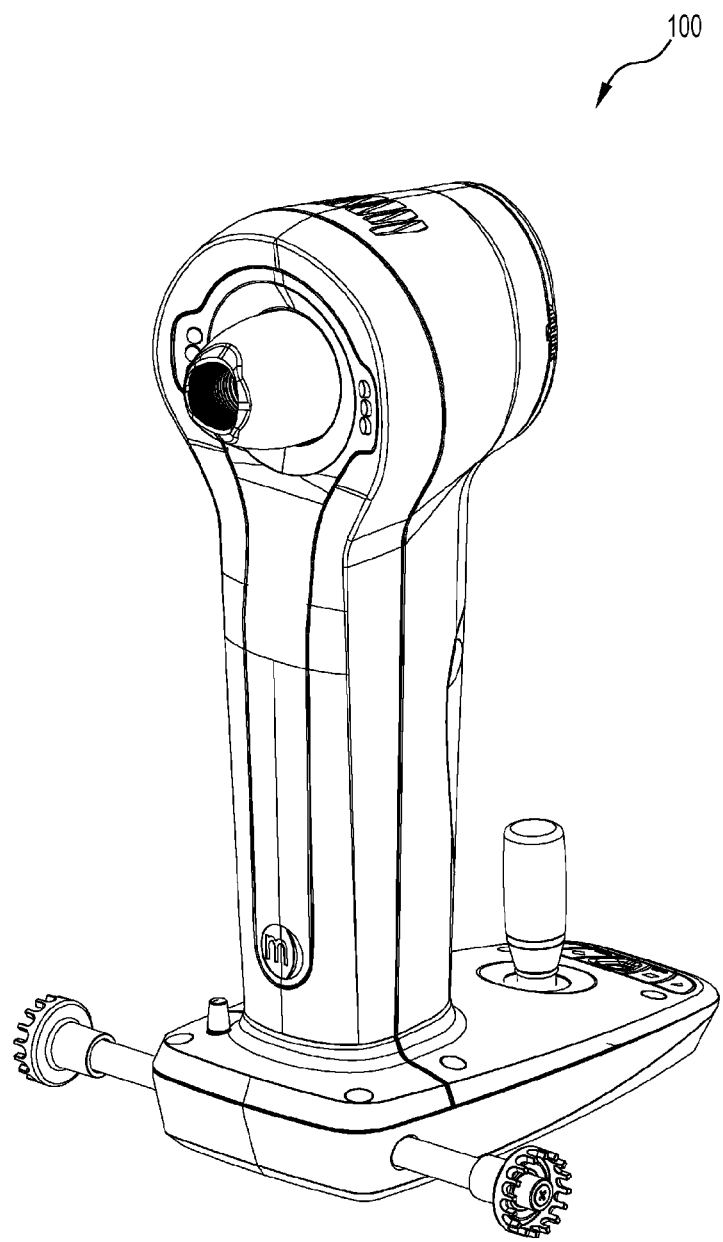
FIGS. 14A and 14B show a commercial embodiment of a light guide and topographer according to the invention.
Figure 14B:
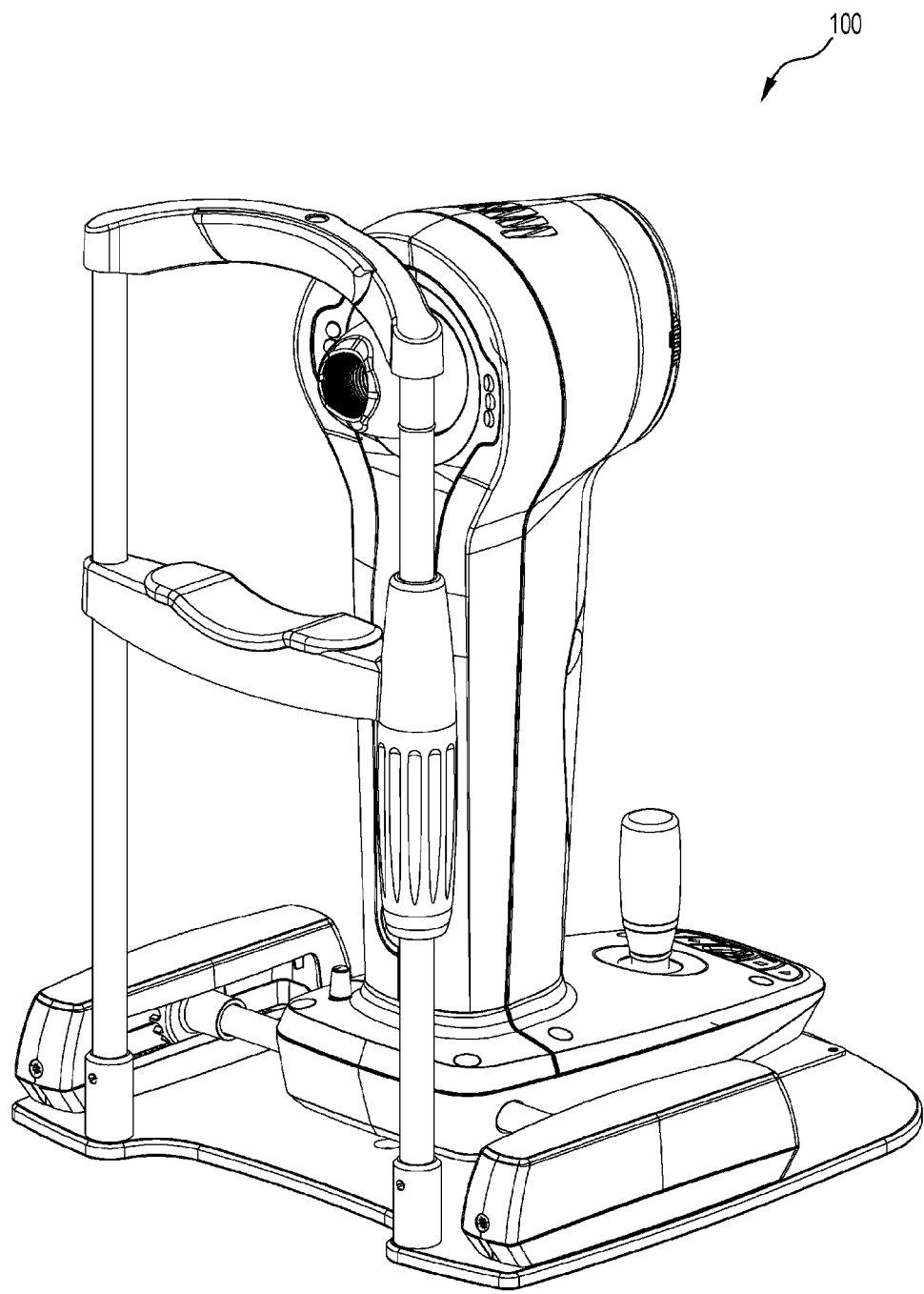

The registration diaphragm 423 comprises two or more adjacent registration apertures 423a through which light from the scleral reference light source 408 can propagate and be disposed onto cornea 107. In the embodiment shown, the two or more adjacent registration apertures 423a comprise respective sets of one or two or more adjacent transparent round dots. In other embodiments, the adjacent registration apertures 423a comprise a set or two or more adjacent transparent and opaque alternating rings concentric to the axis of the central channel 124, forming a second Placido disk 416. As shown in FIG. 13, the two or more adjacent registration apertures 423a comprise three transparent circular rings. In yet another embodiment, the circular rings may be used as a reference diaphragm and can be used together with the alternating circular rings 418.

The projected scleral aperture pattern 405 on the eye surface and the registration diaphragm 423 may be imaged together on the same image onto the one or more capture system 113. From such two adjacent rings or dots of the said registration diaphragm 423, curvature and height information of the reflecting eye surface can be derived.

The scleral measuring device 400 may further apply an algorithm to improve the accuracy of the scleral height information by comparing an eye reference axis of the scleral image 410 to an eye reference axis of a corneal image 204. Said reference axis may contain rotational information of the eye 106 to the axis of the central channel 124 or between the eye 106 and the central channel 122.

In one embodiment, the light guide body and topography illumination source may form the corneal reference object. In a preferred embodiment, the corneal reference object comprises both a corneal reference object projected by the light guide body and topography illumination source for an apical point and the corneal aperture pattern for the for additional corneal reference information.

Advantageously, the pupil 413 may be captured in both the scleral image 410 and corneal image 204 wherein the captured pupil information may provide information of said eye reference axis. In addition, or alternatively, other uniquely identifiable scleral features may be used to combine said corneal and scleral height information.

Also, pupil centre location of the eye 106 relative to the said axis of central channel 124 may be measured to provide reference data for combining said corneal and scleral height information.

The utilisation of the scleral measurement device 400 as part of topographer 100 allows the scleral data to be combined with the corneal topography data. Advantageously, this does not rely on scatter image and instead uses a reflection off the cornea. Additionally, the relative pupil location of both eyes may be measured to provide reference data for image registration.

One advantage of the present invention is that, because the illumination is no longer external to the light guide body 102, the diameter at the proximal end 113 can be reduced. This allows closer proximity of corneal surface 148 to the light guide body 102 and hence analysis of a larger corneal portion.

Another advantage of the present invention is that the illumination no longer causes shadowing that affects the distribution of light. The present invention also greatly reduces the number of components required for illumination and the complexity of manufacture.

In this specification, the terms "comprises", "comprising" or similar terms are intended to mean a non-exclusive inclusion, such that an apparatus that comprises a list of elements does not include those elements solely, but may well include other elements not listed.

Throughout the specification the aim has been to describe the invention without limiting the invention to any one embodiment or specific collection of features. Persons skilled in the relevant art may realize variations from the specific embodiments that will nonetheless fall within the scope of the invention.

The claims defining the invention are as follows:

1. An ophthalmological topographer comprising:
    a corneal topographer; and
    a scleral measurement device comprising one or more scleral projection systems,
    wherein each of the one or more scleral projection systems comprise a scleral reference object comprising at least one diaphragm comprising two or more adjacent registration apertures through which light can propagate and be disposed onto a cornea.

2. The ophthalmological topographer of claim 1, wherein the corneal topographer directs a reference object on an eye surface.

3. The ophthalmological topographer of claim 2, wherein the directed reference object comprises a projected reference object or mires.

4. The ophthalmological topographer of claim 2, comprising an imaging system imaging the reference object directed onto said eye surface through a central channel in the topographer body.

5. The ophthalmological topographer of claim 1, further comprising a topography illumination source.

6. The ophthalmological topographer of claim 1, wherein each of the one or more scleral projection systems comprise a scleral projection light source.

7. The ophthalmological topographer of claim 6, wherein the one or more apertures are disposed in an aperture pattern.

8. The ophthalmological topographer of claim 6, wherein the one or more apertures comprise a scleral aperture pattern.

9. The ophthalmological topographer of claim 8, wherein when imaged on an eye or an imaging sensor, the scleral aperture pattern is imaged as one or more scleral locators.

10. The ophthalmological topographer of claim 8, wherein the scleral aperture pattern illuminated by the scleral projection light source is imaged onto the projection imaging system and onto a scleral portion of an eye surface.

11. The ophthalmological topographer of claim 6, wherein the one or more apertures comprise a corneal aperture pattern.

12. The ophthalmological topographer of claim 11, wherein when imaged on an eye or an imaging sensor, the corneal aperture pattern is imaged as a corneal scatter image.

13. The ophthalmological topographer of claim 11, wherein the corneal aperture pattern illuminated by the projection light source is imaged onto the projection imaging system and onto a cornea.

14. The ophthalmological topographer of claim 6, wherein the one or more apertures comprise a scleral aperture pattern and a corneal aperture pattern.

15. The ophthalmological topographer of claim 1, wherein each of the one or more scleral projection systems further comprise a scleral projection imaging system.

16. The ophthalmological topographer of claim 1, wherein the one or more scleral projection systems are symmetrically mounted on the topographer.

17. The ophthalmological topographer of claim 1, further comprising one or more scleral registration reference object projector.

18. The ophthalmological topographer of claim 17, wherein the scleral registration reference object projector comprises a scleral reference light source and a scleral registration reference object.

19. The ophthalmological topographer of claim 18, wherein the scleral registration reference object projector comprises a registration reference object light guide.

20. The ophthalmological topographer of claim 18, wherein light from the scleral reference light source passing through the scleral registration reference object and reflected from an eye surface forms at least a part of a scleral image.

21. The ophthalmological topographer of claim 20, wherein light from the scleral image is digitally processed to obtain corneal height information and scleral height information.

22. The ophthalmological topographer of claim 21, wherein the processed scleral image is used to combine the corneal height information from the topographer with the scleral height information into a new scleral topographic map.

23. The ophthalmological topographer of claim 22, wherein the projected scleral aperture pattern on the eye surface and the registration diaphragm may be imaged together on a same scleral image onto one or more capture system.

24. The ophthalmological topographer of claim 22, wherein the one or more scleral reference object apertures and/or the scleral registration apertures are imaged on one or more imaging sensor by an imaging system.

25. The ophthalmological topographer of claim 1, further comprising a processor to combine scleral height information acquired from the scleral measurement device and corneal height information from the corneal topographer.

26. The ophthalmological topographer of claim 1, wherein the scleral measuring device further applies an algorithm to improve accuracy of the scleral height information by comparing an eye reference axis of a scleral image to an eye reference axis of a corneal image.

* * * * *